United States Patent [19]

Petre et al.

[11] Patent Number: 5,260,208

[45] Date of Patent: Nov. 9, 1993

[54] ENANTIOSELECTIVE AMIDASES, DNA SEQUENCES ENCODING THEM, METHOD OF PREPARATION AND UTILIZATION

[75] Inventors: Dominique Petre; Edith Cerbelaud, both of Lyon; Jean-François Mayaux, Fontenay-Aux-Roses; Patrice Yeh, Paris, all of France

[73] Assignee: Rhone-Poulenc Sante, Paris, France

[21] Appl. No.: 612,673

[22] Filed: Nov. 14, 1990

[30] Foreign Application Priority Data

Dec. 11, 1989 [FR] France ................. 89 16332

[51] Int. Cl.$^5$ ............ C12N 15/55; C12N 15/74; C12N 15/77; C12N 9/80
[52] U.S. Cl. ................. 435/228; 435/252.3; 435/252.32; 435/320.1; 435/69.1; 536/23.2
[58] Field of Search ........ 435/136, 280, 252.3, 435/252.32, 252.33, 250, 228, 320.1; 536/27, 23.2

[56] References Cited

U.S. PATENT DOCUMENTS

| | | |
|---|---|---|
| 4,514,502 | 4/1985 | Miwa et al. ............ 435/253 |
| 4,816,397 | 3/1989 | Boss et al. ............. 435/68 |
| 4,861,722 | 8/1989 | Sano et al. ............. 435/252.32 |
| 4,920,054 | 4/1990 | Kozlowski et al. ....... 435/252.31 |
| 4,921,699 | 5/1990 | DeChiara et al. ........ 424/85.7 |
| 4,925,799 | 5/1990 | Rosenberg ............. 435/172.3 |
| 4,965,197 | 10/1990 | Liebl et al. ........... 435/69.8 |
| 5,034,329 | 7/1991 | Cerbeland et al. ....... 435/280 |
| 5,089,405 | 2/1992 | Cerbeland et al. ....... 435/136 |

FOREIGN PATENT DOCUMENTS

| | | | |
|---|---|---|---|
| 326482 | 1/1989 | European Pat. Off. ........ 435/280 |
| 2626288 | 2/1988 | France ................. 435/280 |
| 2218985 | 11/1989 | United Kingdom ........... 435/136 |
| 8901525 | 2/1989 | World Int. Prop. O. ...... 435/106 |

OTHER PUBLICATIONS

Lathe, R., 1985, The Journal of Molecular Biology 183:1–12.
Jung, G. et al., 1988, Annales de L'Institute Pasteur; Microbiologie, 139:129–146.
de Boer, H. A. et al., 1983, in *Genes: Structure and Expression*, Kroon, A. M., Ed., John Wiley & Sons, Ltd. pp. 205–248.
Ikehata, M. et al., 1989, European Journal of Biochemistry 181(3):563–570.
Previero A., et al., 1983, Monatshefte für Chemie, 114:1059–1069.
Maestracci, M., et al., 1986, Agricultural and Biological Chemistry, 50(9):2237–2241.
Yeh, P., et al., 1988, *Molecular and General Genetics*, 212(1):105–111.
Thiery, A., et al., 1986, The Journal of General Microbiology, 132(8): 2205–2208.
Vo-Quang, Y., et al., 1987, Tetrahedron Letters 28(35):4057–4060.

Primary Examiner—Robert A. Wax
Assistant Examiner—William W. Moore
Attorney, Agent, or Firm—Finnegan, Henderson, Farabow, Garrett & Dunner

[57] ABSTRACT

The present invention concerns a DNA sequence coding for a polypeptide with enantioselective amidase activity.

20 Claims, 18 Drawing Sheets

FIG.1A

N-TERMINAL FRAGMENT
Ala Thr Ile Arg Pro Asp Asp Lys Ala Ile Asp Ala Ala Ala
Arg His Tyr Gly Ile Thr Leu Asp Lys Thr Ala (Arg) Leu ...

INTERNAL FRAGMENT
Leu Glu Trp Pro Ala Leu Ile (Asp) Gly Ala Leu
Gly Ser Tyr Asp Val Val Asp Gln Leu Tyr ...

FIG.1B

```
        IleAspGlyAlaLeuGlySerTyrAspVal
5' - ATCGATGGCGCCCTCGGCTCCTACGATGT. - 3'         CODING STRAND
              A
              G
              T

3'- TAGCTGCCGCGGGAGCCGAGGATGCTGCA - 5'          PROBE (Sq 762)
            C  C
            T
```

FIG.2a

```
           A         T  AT
  48°C                T  AT
           C         T
           A         T  A
                     T  AA
  ---------------------------
           C    ( )  G  T
           A         T  T
  45°C               T
                     C
           C  C  A   C  T
5' CCAAGCTT GCTGTTTTGTCAAGCGT GATGCCGTAATGCCTTGCGGCGGCGTCTATTGCTTTGTC
3'          CGACAAAACAGTTCGCA CTACGGCATTACGGAACGCCGCCGCAGATAACGAAACAG
            ThrLysAspLeuThrIleGlyTyrHisArgAlaAlaAlaAspIleAlaLysAsp
                                                        <---------

G  A       T
         G  A  G    C   G
  48°C   G  A
         G     G
         G  G
  ---------------------------
         G  G       C
         A          G
  45°C   G     A
         A  C    CTAAG
         A  G  G
         GTCTGGTCGAATGGTAGC         3'
         CAGACCAGCTTACCATCGCTTAAGGC 5'
         AspProArgIleThrAla
```

FIG.2b

```
5'                                              3'
GATGCGGTAATGCCTTGCGGCGGCGTCTATTGCTTTGTCG     SPECIFIC PROBE
                                                 (Sq918)
```

FIG.3A
Sq 918
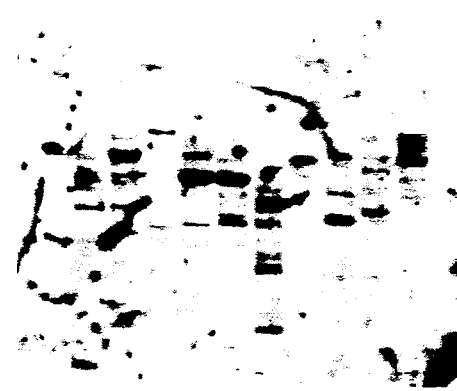
Sq 762
Prehybridization ~5h à 55°C
hybridization ~18h à 55°C
FIG.3B

```
cgatccggaaacagtacttcggcagcttgccacgacaccgaaaagctctacgaacaccggtgttccactgca        72 tcggccgattctgatcgctgaatcggcccgtgggcgactgtaccccgctctctctgagcgcacgtaacccg       144
                                                            BamHI
aacttaacgagtcaatatgtcgatacctattgacgcaattatggatccggccctagtctgaaagacaagtga      216
                 SD                  amidase  ———▶
agccgatcacatcaggagcacacttctc ATG GCG ACA ATC CGA CCT GAC GAC AAA GCA ATA       277
                             Met Ala Thr Ile Arg Pro Asp Asp Lys Ala Ile       11

GAC GCC GCC GCA AGG CAT TAC GGC ATC ACT CTC GAC AAA ACA GCC CGG CTC GAG        331
Asp Ala Ala Ala Arg His Tyr Gly Ile Thr Leu Asp Lys Thr Ala Arg Leu Glu         29

TGG CCG GCA CTG ATC GAC GGA GCA CTG GGC TCC TAC GAC GTC GTC GAC CAG TTG        385
Trp Pro Ala Leu Ile Asp Gly Ala Leu Gly Ser Tyr Asp Val Val Asp Gln Leu         47

TAC GCC GAC GAG GCG ACC CCG CCG ACC ACG TCA CGC GAG CAC GCG GTG CCA AGT        439
Tyr Ala Asp Glu Ala Thr Pro Pro Thr Thr Ser Arg Glu His Ala Val Pro Ser         65

GCG AGC GAA AAT CCT TTG AGC GCT TGG TAT GTG ACC ACC AGC ATC CCG CCG ACG        493
Ala Ser Glu Asn Pro Leu Ser Ala Trp Tyr Val Thr Thr Ser Ile Pro Pro Thr         83

TCG GAC GGC GTC CTG ACC GGC CGA CGC GTG GCG ATC AAG GAC AAC GTG ACC GTG        547
Ser Asp Gly Val Leu Thr Gly Arg Arg Val Ala Ile Lys Asp Asn Val Thr Val        101

GCC GGA GTT CCG ATG ATG AAC GGA TCT CGG ACG GTA GAG GGA TTT ACT CCG TCA        601
Ala Gly Val Pro Met Met Asn Gly Ser Arg Thr Val Glu Gly Phe Thr Pro Ser        119

CGC GAC GCG ACT GTG GTC ACT CGA CTA CTG GCG GCC GGT GCA ACC GTC GCG GGC        655
Arg Asp Ala Thr Val Val Thr Arg Leu Leu Ala Ala Gly Ala Thr Val Ala Gly        137

AAA GCT GTG TGT GAG GAC CTG TGT TTC TCC GGT TCG AGC TTC ACA CCG GCA AGC        709
Lys Ala Val Cys Glu Asp Leu Cys Phe Ser Gly Ser Ser Phe Thr Pro Ala Ser        155

GGA CCG GTC CGC AAT CCA TGG GAC CGG CAG CGC GAA GCA GGT GGA TCA TCC GGC        763
Gly Pro Val Arg Asn Pro Trp Asp Arg Gln Arg Glu Ala Gly Gly Ser Ser Gly        173

GGC AGT GCA GCA CTC GTC GCA AAC GGT GAC GTC GAT TTT GCC ATC GGC GGG GAT        817
Gly Ser Ala Ala Leu Val Ala Asn Gly Asp Val Asp Phe Ala Ile Gly Gly Asp        191

CAA GGC GGA TCG ATC CGG ATC CCG GCG GCA TTC TGC GGC GTC GTC GGG CAC AAG        871
Gln Gly Gly Ser Ile Arg Ile Pro Ala Ala Phe Cys Gly Val Val Gly His Lys        209

CCG ACG TTC GGG CTC GTC CCG TAT ACC GGT GCA TTT CCC ATC GAG CGA ACA ATC        925
Pro Thr Phe Gly Leu Val Pro Tyr Thr Gly Ala Phe Pro Ile Glu Arg Thr Ile        227

GAC CAT CTC GGC CCG ATC ACA CGC ACG GTC CAC GAT GCA GCA CTG ATG CTC TCG        979
Asp His Leu Gly Pro Ile Thr Arg Thr Val His Asp Ala Ala Leu Met Leu Ser        245

GTC ATC GCC GGC CGC GAC GGT AAC GAC CCA CGC CAA GCC GAC AGT GTC GAA GCA       1033
Val Ile Ala Gly Arg Asp Gly Asn Asp Pro Arg Gln Ala Asp Ser Val Glu Ala        263
```

FIG.8A

```
GGT GAC TAT CTG TCC ACC CTC GAC TCC GAT GTG GAC GGC CTG CGA ATC GGA ATC   1087
Gly Asp Tyr Leu Ser Thr Leu Asp Ser Asp Val Asp Gly Leu Arg Ile Gly Ile    281

GTT CGA GAG GGA TTC GGG CAC GCG GTC TCA CAG CCC GAG GTC GAC GAC GCA GTC   1141
Val Arg Glu Gly Phe Gly His Ala Val Ser Gln Pro Glu Val Asp Asp Ala Val    299

CGC GCA GCG GCA CAC AGT CTG ACC GAA ATC GGT TGC ACG GTA GAG GAA GTA AAC   1195
Arg Ala Ala Ala His Ser Leu Thr Glu Ile Gly Cys Thr Val Glu Glu Val Asn    317
                     Sph I
ATC CCG TGG CAT CTG CAT GCT TTC CAC ATC TGG AAC GTG ATC GCC ACG GAC GGT   1249
Ile Pro Trp His Leu His Ala Phe His Ile Trp Asn Val Ile Ala Thr Asp Gly    335

GGT GCC TAC CAG ATG TTG GAC GGC AAC GGA TAC GGC ATG AAC GCC GAA GGT TTG   1303
Gly Ala Tyr Gln Met Leu Asp Gly Asn Gly Tyr Gly Met Asn Ala Glu Gly Leu    353

TAC GAT CCG GAA CTG ATG GCA CAC TTT GCT TCT CGA CGC ATT CAG CAC GCC GAC   1357
Tyr Asp Pro Glu Leu Met Ala His Phe Ala Ser Arg Arg Ile Gln His Ala Asp    371

GCT CTG TCC GAA ACC GTC AAA CTG GTG GCC CTG ACC GGC CAC CAC GGC ATC ACC   1411
Ala Leu Ser Glu Thr Val Lys Leu Val Ala Leu Thr Gly His His Gly Ile Thr    389

ACC CTC GGC GGC GCG AGC TAC GGC AAA GCC CGG AAC CTC GTA CCG CTT GCC CGC   1465
Thr Leu Gly Gly Ala Ser Tyr Gly Lys Ala Arg Asn Leu Val Pro Leu Ala Arg    407

GCC GCC TAC GAC ACT GCC TTG AGA CAA TTC GAC GTC CTG GTG ATG CCA ACG CTG   1519
Ala Ala Tyr Asp Thr Ala Leu Arg Gln Phe Asp Val Leu Val Met Pro Thr Leu    425

CCC TAC GTC GCA TCC GAA TTG CCG GCG AAG GAC GTA GAT CGT GCA ACC TTC ATC   1573
Pro Tyr Val Ala Ser Glu Leu Pro Ala Lys Asp Val Asp Arg Ala Thr Phe Ile    443

ACC AAG GCT CTC GGG ATG ATC GCC AAC ACG GCA CCA TTC GAC GTG ACC GGA CAT   1627
Thr Lys Ala Leu Gly Met Ile Ala Asn Thr Ala Pro Phe Asp Val Thr Gly His    461

CCG TCC CTG TCC GTT CCG GCC GGC CTG GTG AAC GGG CTT CCG GTC GGA ATG ATG   1681
Pro Ser Leu Ser Val Pro Ala Gly Leu Val Asn Gly Leu Pro Val Gly Met Met    479

ATC ACC GGC AGA CAC TTC GAC GAT GCG ACA GTC CTT CGT GTC GGA CGC GCA TTC   1735
Ile Thr Gly Arg His Phe Asp Asp Ala Thr Val Leu Arg Val Gly Arg Ala Phe    497
     Hind III
GAA AAG CTT CGC GGC GCG TTT CCG ACG CCG GCC GAA CGC GCC TCC AAC TCT GCA   1789
Glu Lys Leu Arg Gly Ala Phe Pro Thr Pro Ala Glu Arg Ala Ser Asn Ser Ala    515

CCA CAA CTC AGC CCC GCC tagtcctgacgcactgtcagacaacaaattccaccgattcacacatg  1854
Pro Gln Leu Ser Pro Ala                                                    521 atcagcccacataagaaaaggtgaa
```

FIG.8B

S: Supernatants
T: Total
C: Pellet
M: Marker pxL 1029: IL1β under control of PRcIts
pxL 906:    "        "        "     Ptrp

```
BamHI,SalI,PstI (polylinker)
ctgcagaacggaactaagatggctcgaaccttcaccaaagacggacttgaacacagcctcgcacttgcgcgt    72 ttggagctcccggacgagcgttacgagacggtgacagcggctgccgagttggtcctcggactcgctgaggct   144

NdeI
                                                                    cat
ctggatgctgtcccgctggccgagactccgatggcagccgccttcgatgcgcggtgggagtgacg ATG      212
                                                                    Met      1
```

| | | | | | | | | | | | | | | | | | | |
|---|---|---|---|---|---|---|---|---|---|---|---|---|---|---|---|---|---|---|
| GGC | TTG | CAT | GAA | CTG | ACG | CTC | GCG | CAA | GTC | GCT | GCG | AAG | ATC | GAG | AAC | AAA | GAA | 266 |
| Gly | Leu | His | Glu | Leu | Thr | Leu | Ala | Gln | Val | Ala | Ala | Lys | Ile | Glu | Asn | Lys | Glu | 19 |
| CTT | TCC | CCG | GTC | GAG | CTC | CTC | GAT | GTG | ATC | CTG | GCG | CGC | GTC | GCG | GAG | ATC | GAA | 320 |
| Leu | Ser | Pro | Val | Glu | Leu | Leu | Asp | Val | Ile | Leu | Ala | Arg | Val | Ala | Glu | Ile | Glu | 37 |
| CCG | AAG | ATC | TCC | GCC | TTC | GTC | ACG | ATC | ACC | GCC | GAT | TCC | GCT | CGG | AAG | GCG | GCC | 374 |
| Pro | Lys | Ile | Ser | Ala | Phe | Val | Thr | Ile | Thr | Ala | Asp | Ser | Ala | Arg | Lys | Ala | Ala | 55 |
| CGG | CTC | GCA | GCC | GAC | GAG | ATC | GCA | GGT | GGG | CAC | TAT | CGC | GGT | CCG | CTG | CAC | GGA | 428 |
| Arg | Leu | Ala | Ala | Asp | Glu | Ile | Ala | Gly | Gly | His | Tyr | Arg | Gly | Pro | Leu | His | Gly | 73 |
| GTT | CCG | ATT | GGC | CTC | AAG | GAT | CTG | TTC | GAA | GTG | GCA | GGC | GTC | CCG | AAT | ACC | GCG | 482 |
| Val | Pro | Ile | Gly | Leu | Lys | Asp | Leu | Phe | Glu | Val | Ala | Gly | Val | Pro | Asn | Thr | Ala | 91 |
| AGT | TCG | CGG | GTC | CGA | GCT | GAC | TAC | ATC | CCC | TCA | TCG | GAT | GGG | GCC | GCG | GTC | GAG | 536 |
| Ser | Ser | Arg | Val | Arg | Ala | Asp | Tyr | Ile | Pro | Ser | Ser | Asp | Gly | Ala | Ala | Val | Glu | 109 |
| AAG | CTC | ACC | GCC | GGT | GGA | GCG | GTC | ATG | ATC | GGC | AAG | ACG | CAC | ACT | CAC | GAA | TTC | 590 |
| Lys | Leu | Thr | Ala | Gly | Gly | Ala | Val | Met | Ile | Gly | Lys | Thr | His | Thr | His | Glu | Phe | 127 |
| GCC | TAC | GGT | GCG | ATC | ACA | CCG | ACC | ACC | CGT | AAT | CCA | TGG | GAC | CCC | ACC | CGG | ACA | 644 |
| Ala | Tyr | Gly | Ala | Ile | Thr | Pro | Thr | Thr | Arg | Asn | Pro | Trp | Asp | Pro | Thr | Arg | Thr | 145 |
| CCC | GGC | GGT | TCC | AGC | GGT | GGG | ACG | GCA | GCA | GCT | CTC | GCG | GCA | GGC | CTC | ATC | TTC | 698 |
| Pro | Gly | Gly | Ser | Ser | Gly | Gly | Thr | Ala | Ala | Ala | Leu | Ala | Ala | Gly | Leu | Ile | Phe | 163 |
| GCC | GGT | ATG | GGT | ACC | GAT | ACC | GGG | GGG | TCC | ATT | CGG | ATA | CCA | GCC | GCC | GTC | TGC | 752 |
| Ala | Gly | Met | Gly | Thr | Asp | Thr | Gly | Gly | Ser | Ile | Arg | Ile | Pro | Ala | Ala | Val | Cys | 181 |
| GGG | ACG | GTA | GGT | CTC | AAA | CCC | ACA | TAT | GGT | CGC | GTT | TCG | CGT | CGT | GGA | GTG | ACC | 806 |
| Gly | Thr | Val | Gly | Leu | Lys | Pro | Thr | Tyr | Gly | Arg | Val | Ser | Arg | Arg | Gly | Val | Thr | 199 |
| TCC | TTG | TCA | TGG | TCT | CTG | GAC | CAC | GCG | GGA | CCG | CTG | GCC | CGG | ACC | GTG | GAA | GAC | 860 |
| Ser | Leu | Ser | Trp | Ser | Leu | Asp | His | Ala | Gly | Pro | Leu | Ala | Arg | Thr | Val | Glu | Asp | 217 |
| GCT | GCC | ATC | ATG | CTG | AAC | CAG | ATC | GCT | GGC | TAT | GAC | CGG | GCT | GAT | CCT | GCG | ACG | 914 |
| Ala | Ala | Ile | Met | Leu | Asn | Gln | Ile | Ala | Gly | Tyr | Asp | Arg | Ala | Asp | Pro | Ala | Thr | 235 |
| GTA | GAT | GTG | CCC | GTT | CCC | GAC | TAC | GCG | GCG | GCG | CTG | ACC | GGA | GAC | GTC | CGA | GGG | 968 |
| Val | Asp | Val | Pro | Val | Pro | Asp | Tyr | Ala | Ala | Ala | Leu | Thr | Gly | Asp | Val | Arg | Gly | 253 |

```
CTG CGG ATT GGT GTG CCG ACC AAT TTC TAC ACC GAC AAC GTC CAT CCC GAG GTT   1022
Leu Arg Ile Gly Val Pro Thr Asn Phe Tyr Thr Asp Asn Val His Pro Glu Val    271

GCC GCA GCG GCC GAC GCT GCG GTG GCG CAA CTG GCC CAT TTG GGT GCG GTG GTC   1076
Ala Ala Ala Ala Asp Ala Ala Val Ala Gln Leu Ala His Leu Gly Ala Val Val    289

CGC GAA GTG AAG ATC CCG ATG GCA GAG GTC ATC GTG CCC ACC GAG TGG AGC TTG   1130
Arg Glu Val Lys Ile Pro Met Ala Glu Val Ile Val Pro Thr Glu Trp Ser Leu    307

CTC GTC CCG GAG GCG TCG GCC TAC CAC CAG CAG ATG CTG CGC GAG CGC GCA GAT   1184
Leu Val Pro Glu Ala Ser Ala Tyr His Gln Gln Met Leu Arg Glu Arg Ala Asp    325

CAC TAC ACC GAC GAG ACG AGA ACC TTC CTG GAA GCC GGC GAA CTC GTT CCG GCG   1238
His Tyr Thr Asp Glu Thr Arg Thr Phe Leu Glu Ala Gly Glu Leu Val Pro Ala    343

ACC GAC TAC ATC AAG GCG CTG CGG GTG CGC ACC CTC ATC CAG GCA GCC TTC CGG   1292
Thr Asp Tyr Ile Lys Ala Leu Arg Val Arg Thr Leu Ile Gln Ala Ala Phe Arg    361

GAA CTG TTC CAG GAC ATC GAT GTC CTG ATC GCA CCC ACG GTC AGC TCT CCG GCT   1346
Glu Leu Phe Gln Asp Ile Asp Val Leu Ile Ala Pro Thr Val Ser Ser Pro Ala    379

CTG CCG CTC GAT GAC CTG GAA GTC ACT TGG CCC GAT GGC ACA TCC GAA GGC GGC   1400
Leu Pro Leu Asp Asp Leu Glu Val Thr Trp Pro Asp Gly Thr Ser Glu Gly Gly    397

ACC ATC ACC TAT GTC CGT CTC AGC GCC CCC GGC AAC GTC ACC GGA CTT CCA GCG   1454
Thr Ile Thr Tyr Val Arg Leu Ser Ala Pro Gly Asn Val Thr Gly Leu Pro Ala    415

CTG TCG GTC CCC TCC GGC TTC ACC GAG CAA GGC CTT CCC ACC GGT ATC CAG ATC   1508
Leu Ser Val Pro Ser Gly Phe Thr Glu Gln Gly Leu Pro Thr Gly Ile Gln Ile    433

ATC GGC CGT CCC TTC GAC GAG GAG ACC GTC CTC AAC GTC GGT CAC GCC TAC GAA   1562
Ile Gly Arg Pro Phe Asp Glu Glu Thr Val Leu Asn Val Gly His Ala Tyr Glu    451

GGC TGC ACG GAC TGG CCG CGA CTG GCG CCG CTT TGA  actactgacccccattggagaaa  1621
Gly Cys Thr Asp Trp Pro Arg Leu Ala Pro Leu                                463
                                                                SalI
accgaaggagagaacgatgaatggagtgttcgatttgggtgggaccgacggcatcggcccggtcgaccctcc  1693 cgctgaagaaccggtgttccgcgcggactgggagaaagcagccttcaccatgttctcggcgctattccgtgc  1765
                                           BamHI
cggctggttcggcatcgacgaattccgtcacggtgtcgaaaagatggatcc
```

FIG. 13-2

ENANTIOSELECTIVE AMIDASES, DNA SEQUENCES ENCODING THEM, METHOD OF PREPARATION AND UTILIZATION

The present invention concerns polypeptides that possess an enantioselective amidase activity. It also concerns the genetic material required for the expression of these polypeptides as well as a microbiological procedure for their preparation. Finally, this invention concerns the utilization of these polypeptides and of transformed microorganisms for the enantioselective synthesis of acids from racemic amides, and in particular propionic acids, especially (S)-2-aryl-propionic acids and (R)-2-aryloxy-propionic acids.

Due to the presence of an asymmetric carbon atom, numerous molecules posses two distinct stereoisomeric forms, R and S, one being a mirror image of the other. This is the case for the 2-aryl-propionic acids. Most of the time, these molecules exist as a racemic mixture, with the two isomers present in more or less equal proportions. In certain cases, only one specific isomer is required, and it is therefore practical to have a means of separating the two isomers, or of performing a stereospecific synthesis of the desired isomer.

The present invention concerns the domain of polypeptides capable of hydrolyzing amides in an enantioselective manner: in particular, racemic 2-aryl-propionamides to (S)-2-aryl-propionic acids, and racemic 2-aryloxy-propionamides to (R)-2-aryloxy-propionic acids.

Among the microorganisms in which this enzymatic activity has been demonstrated, strains of the genus Brevibacterium and Corynebacterium stand out (European patent No. 89 400197.3), and in particular, Brevibacterium strain R312 (CBS 717.73). In addition, strains such as Rhodococcus possess this enzymatic activity.

The present invention involves the characterization and purification of these enantioselective amidase activities, as well as the cloning and sequencing of the genetic material responsible for their expression. In that which follows, the term "Amd" is used to designate all enantioselective amidase activities. The term "Amd sequence" designates all nucleotide sequences coding for said amidase activities.

In particular, the objective of the present invention is to obtain high levels of expression of these enantioselective amidases in different host organisms by using recombinant DNA techniques.

One of the goals of the invention therefore concerns the DNA sequences coding for these polypeptides with enantioselective amidase activity, especially with regard to racemic 2-aryl-propionamides. In a preferred embodiment of the invention, the object concerns the nucleotide sequence coding for the enantioselective amidase of Brevibacterium R312 (represented in FIG. 8) or the enantioselective amidase of Rhodococcus (represented in FIG. 13), as well as any degenerated sequences coding for the same polypeptide. The invention also concerns the sequences that hybridize with these DNA sequences or with fragments thereof and which code for polypeptides with enantioselective amidase activity. The invention also concerns the genes containing these DNA sequences.

Studies of the homology between the peptide sequences of these amidases reveal a highly conserved region responsible for the observed activity. This region corresponds to amino acids 137 to 193 of the peptide sequence shown in FIG. 13 (nucleotides 618 to 788), and to amino acids 159 to 215 of the peptide sequence of the amidase of Brevibacterium R312 previously described, with which it shares a strict homology (67%).

One of the objects of the present invention therefore concerns a DNA sequence such as that described previously, characterized by the fact that it contains at least the sequence coding for amino acids 137 to 193 in FIG. 13, or 159 to 215 in FIG. 8, or a peptide sequence with at least 50% homology to these.

In particular, one of the objects of the present invention concerns a DNA sequence characterized in that it contains all or part of the Amd sequence presented in FIGS. 8 and 13, or a variant thereof. For the purposes of the present invention, "variant" is meant to describe all sequences coding for a polypeptide with enantioselective amidase activity, even if they contain alterations resulting from, for example, mutations, deletions, insertions, or degeneracy of the genetic code.

More precisely, the DNA sequence contains the sequence presented in FIGS. 8 or 13.

These sequences can be obtained by diverse methods. The general strategy is to clone the genomic DNA fragment coding for the desired polypeptide, with the aid of nucleotide probes derived from the purified polypeptide. By using different methods including primer elongation, restriction enzymes, insertion of adaptors, or ligation of linker oligonucleotides, a nucleotide insert containing the desired DNA sequence can be constructed. It can then be mapped and sequenced by techniques described in the literature.

Other techniques can be used as well, including the utilization of DNA and/or partial or total chemical synthesis. These techniques are well known, and the structures described in FIGS. 8 and 13 allow the isolation of an equivalent sequence, in any microorganism, using classical techniques.

In effect, having demonstrated the homology between the different enantioselective amidases, the present invention allows for the production of probes that can serve to identify hybridizing genes (i.e., genes with a sufficient homology) in any genomic bank. It is then easy to verify that such genes code for an enantioselective amidase. In this manner, it is possible to obtain high quantities of amidase in any microorganism. It is also possible that novel enantioselective amidase activities will be revealed.

The present invention also concerns the polypeptides possessing an enantioselective amidase activity, that contain at least one of the following peptide sequences:

sequences corresponding to amino acids 137 to 193 in FIG. 13 sequences corresponding to amino acids 159 to 215 in FIG. 8 sequences sharing at least 50% homology with these sequences.

Another object of the invention concerns novel polypeptides whose structure is derived from the DNA sequences previously described, and which possess an enantioselective amidase activity. These polypeptides are obtained by extraction and purification from cultures of natural or recombinant microorganisms. The purification is carried out in a succession of steps consisting of the preparation of crude extract from the culture, ammonium sulfate fractionation of the extract, and purification by chromatography and gel filtration. Details are given in the examples.

More precisely, the invention concerns the enantioselective amidases of Brevibacterium R312 and Rhodococcus.

The invention also concerns transformed microorganisms containing at least one expression cassette for the DNA sequences mentioned above. These cassettes will preferably be comprised of a DNA sequence according to the present invention, placed under the control of regulatory DNA sequences that insure its expression in the desired host. The cassette can be integrated in the host genome, or inserted in a plasmid carrying a selectable marker and an origin of replication functional in the host.

One of the interests of the present invention is the expression of these polypeptides under artificial conditions, i.e. the expression of a heterologous sequence in a certain cell whose culture conditions are particularly advantageous, and/or the expression of a homologous sequence under the control of at least partially heterologous regulatory signals in order to increase the production and/or ameliorate the culture conditions.

The DNA sequences controlling the expression of the DNA sequences that are the object of the present invention preferably carry a transcription and translation initiation region. This region contains a promoter and a ribosome binding site that can be homologous or heterologous to that of the peptide product.

The choice of regulatory region depends on the host to be used. In particular, for prokaryotic hosts, the heterologous promoter can be chosen from among the strong bacterial promoters, such as the promoters of the tryptophan operon Ptrp, the lactose operon Plac, the right or left promoters of bacteriophage lambda $P_R$ and $P_L$, the strong promoters of corynebacteria phages, or even homologous promoters of corynebacteria. More precisely, in the case of the right promoter of lambda, the temperature sensitive form $P_R$cIts is preferable. For eukaryotic organisms such as yeast, the promoters of the yeast glycolytic genes can be used, such as the promoters of the genes phosphoglycerate kinase (PGK), glyceraldehyde-3-phosphate dehydrogenase (GPD), lactase (LAC4) and enolase (ENO).

When the host microorganism is prokaryotic, the sites of ribosome fixation will preferentially be derived from either the cII gene of lambda or from homologous genes of corynebacteria.

A transcription and translation termination region functional in the host will be placed 3' to the coding sequence. The plasmid will also carry one or several markers permitting a selection of the recombinant host. Dominant markers are preferred, such as those conferring resistance to antibiotics like ampicillin or streptomycin, or to other toxins.

The host microorganisms to be used notably include enterobacteria such as *E. coli*, and corynebacteria of the genus Corynebacterium, Brevibacterium, or Rhodococcus.

Of course, other cell types can be used, based on the same principle.

One object of the invention concerns the plasmids previously described containing at the least a transcription and translation initiation region, a DNA sequence coding for the desired polypeptide, and a selectable marker.

The invention also concerns the transformed microorganisms previously described, regarding their application in the preparation of enantioselective amidases as well as their use for enantioselective synthesis of acids from racemic amides.

The procedure for preparation of enantioselective amidases involves cultivation of the previously described microorganisms under conditions allowing expression of the sequence coding for the enantioselective amidase, followed by separation of the microorganisms from the amidase that has been produced.

More precisely, the invention concerns the utilization of the recombinant microorganisms or polypeptides already described, for the enantioselective synthesis of 2-aryl-propionic acids from the corresponding racemic 2-aryl-propionamides.

According to one of the preferred embodiments of the present invention, a recommended procedure is described that consists of the preparation of a stereoisomer of an organic acid from the corresponding racemic amide, characterized in that the racemic amide is placed in the presence of the microorganism transformed as previously described, or in the presence of a polypeptide obtained as previously described, and the resulting stereoisomer is recovered.

Among the amides that can be subjected to this process, the racemic amide of ketoprofen should be mentioned, from which S(+) ketoprofen—useful in the pharmaceutical industry—can be prepared.

The examples and figures that follow present other characteristics and advantages of the present invention. These should be considered as illustrative and non-limiting.

DESCRIPTION OF FIGURES

FIG. 1:

A. Peptide sequences (N-terminal and internal) obtained from the purified amidase from Brevibacterium R312.

B. Oligonucleotide probe derived from the internal peptide fragment.

FIG. 2:

A. Strategy for the design of probe Sq 918, from the N-terminal peptide fragment derived from the amidase of Brevibacterium R312.

B. Specific probe Sq 918.

FIG. 3:

A. Hybridization profile of probe Sq 918 with total genomic DNA from Brevibacterium R312 digested with EcoRI, HindIII, KpnI, PstI SmaI and SphI.

B. Hybridization profile of probe Sq 762 with total genomic DNA from Brevibacterium R312 digested with BamHI, BglII, EcoRI, KpnI, PstI, SalI, SmaI, SphI, SstI, and XhoI.

FIG. 4:

Restriction maps of plasmids pXL1650 and pXL1651.

FIG. 5:

Restriction map of the 5.4 kb PstI fragment containing the enantioselective amidase gene of Brevibacterium R312.

FIG. 6:

Sequencing strategy of the BamHI-PstI fragment containing the enantioselective amidase gene of Brevibacterium R312.

FIG. 7:

Analysis of the open reading frames of the sequenced fragment.

FIG. 8-1 and 8-2

Nucleotide and peptide sequences of the enantioselective amidase gene of Brevibacterium R312.

Figure 10:
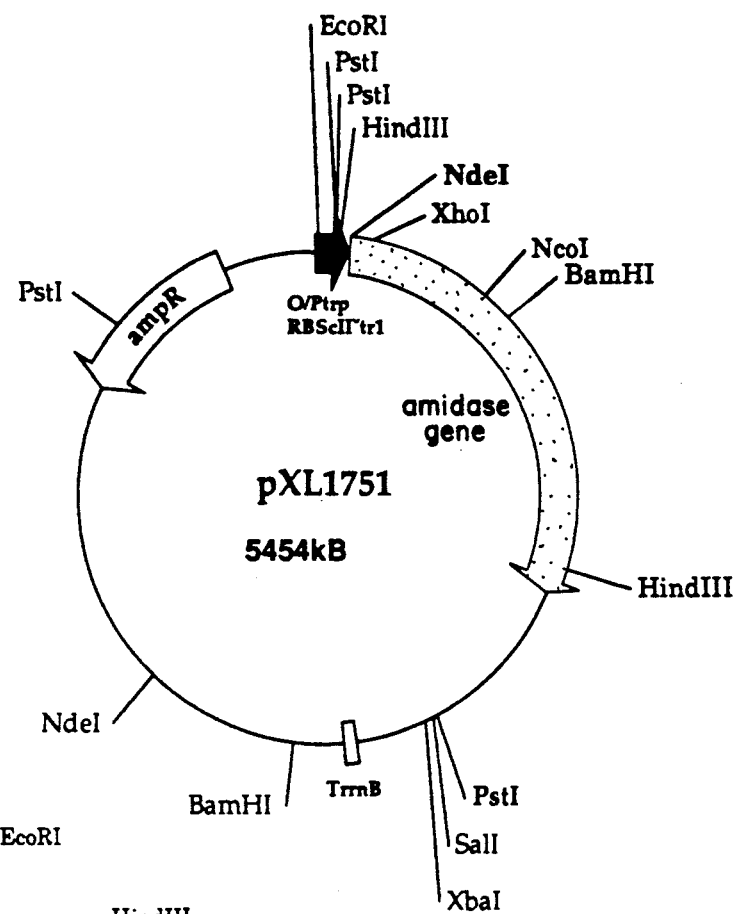
Figure 11:
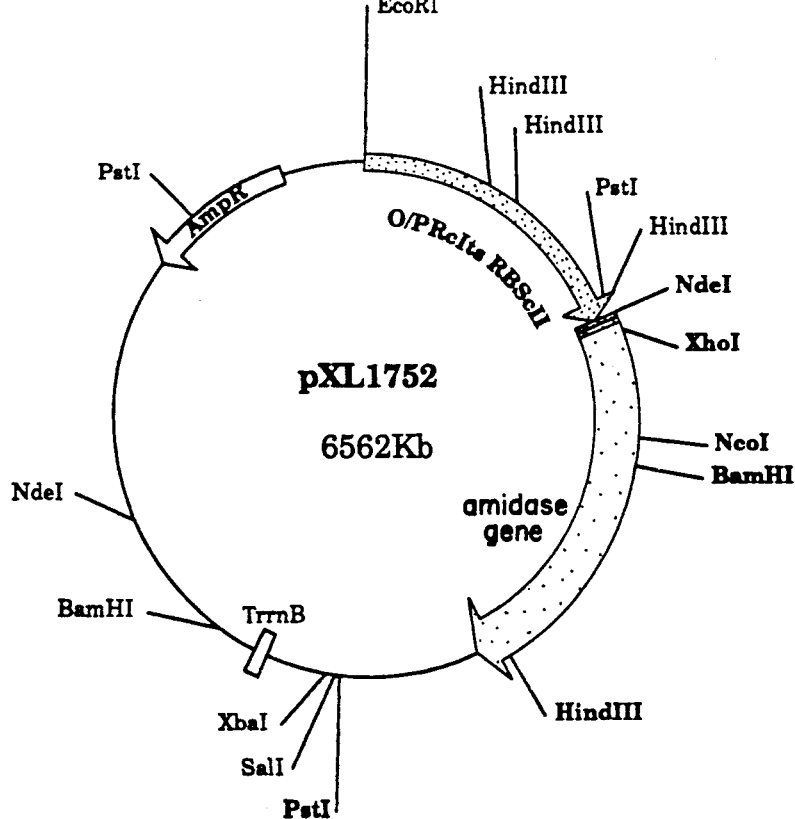
Figure 12:
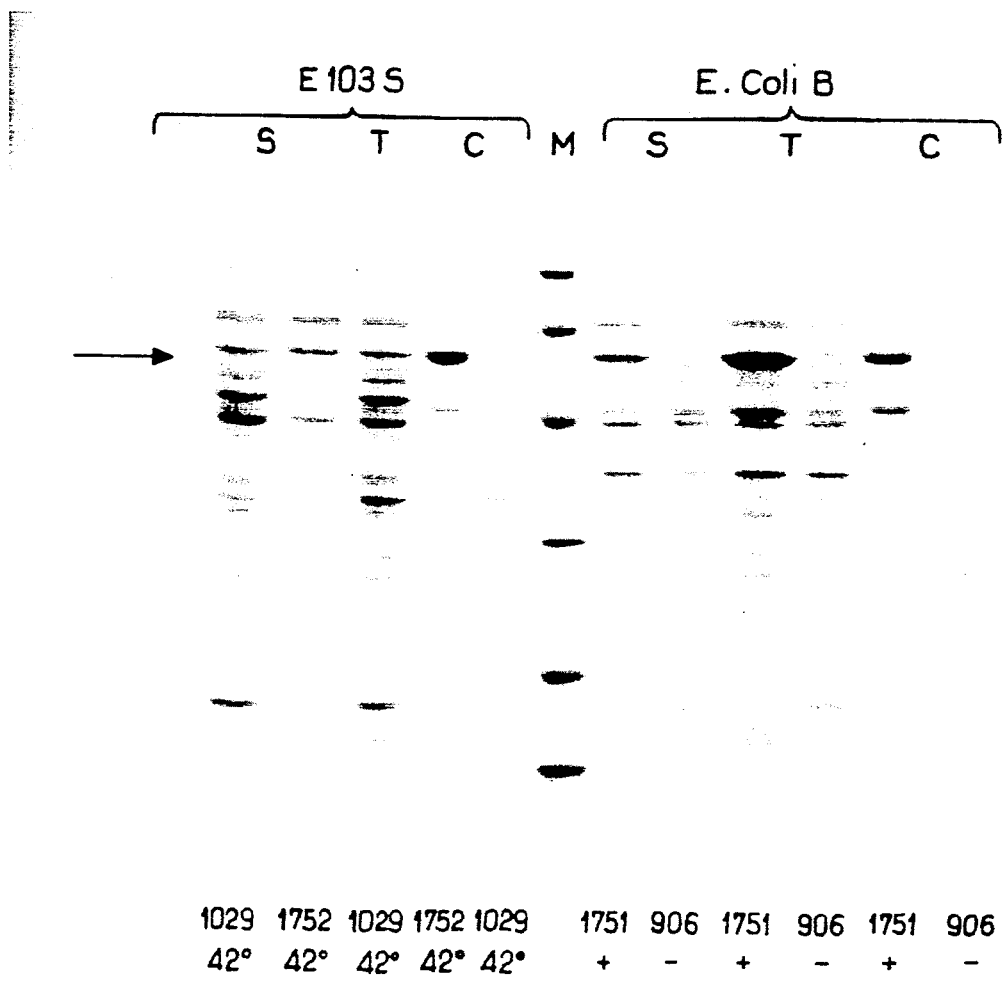

FIG. 9:

Restriction map of plasmid pXL1724.
FIG. 10:
Restriction map of plasmid pXL1751.
FIG. 11:
Restriction map of plasmid pXL1752.
FIG. 12:
12.5% SDS-polyacrylamide gel after Coomassie blue staining, showing the expression of the enantioselective amidase of Brevibacterium R312 in strains *E. coli* B and *E. coli* K12 E103S. Each lane corresponds to a quantity of protein equivalent to 60 μl of the culture at an O.D. of 2.1 (E103S) or 0.7 (*E. coli* B). T, sonicated fraction; S, soluble fraction; C, insoluble fraction. The control plasmids (pXL1029 and pXL906) contain the IL1-β gene under control of the $P_R$cIts or Ptrp promoter, respectively.

Figure 14:
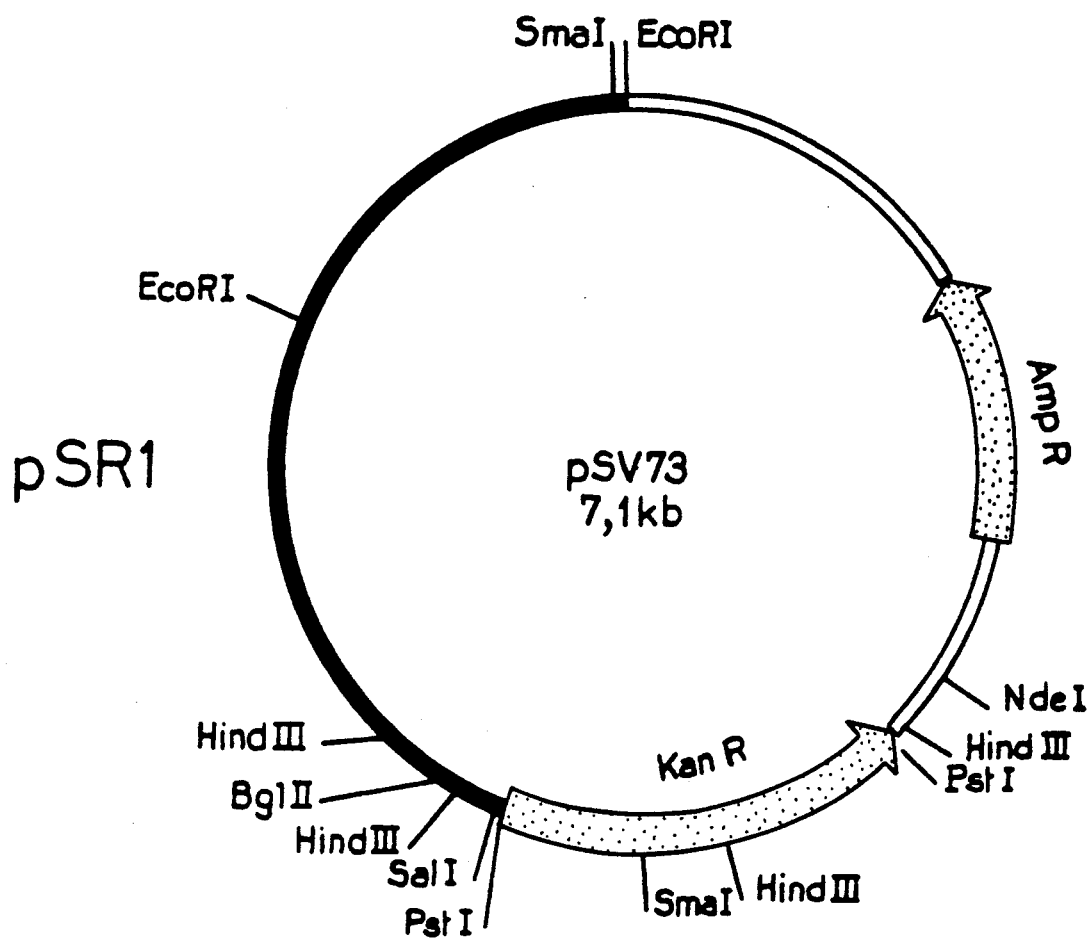
Figure 15:
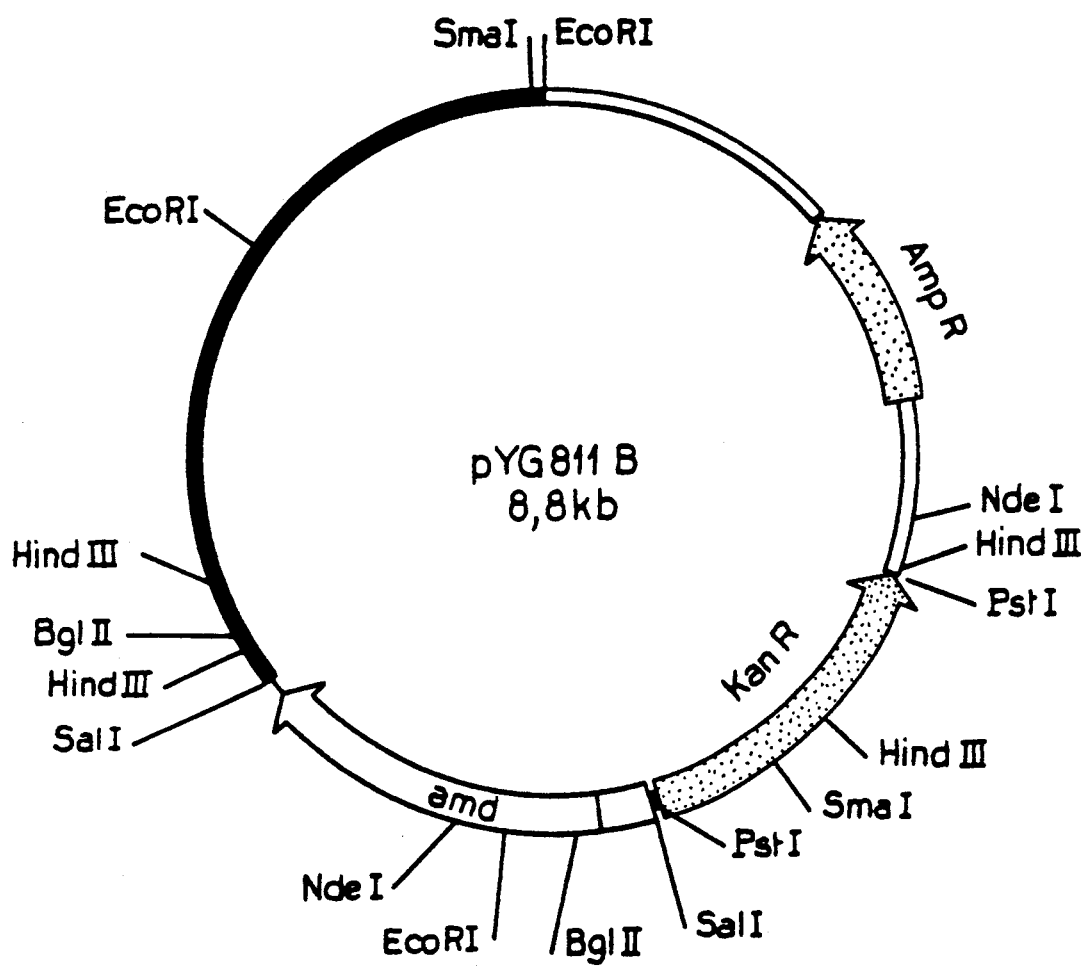
Figure 16:
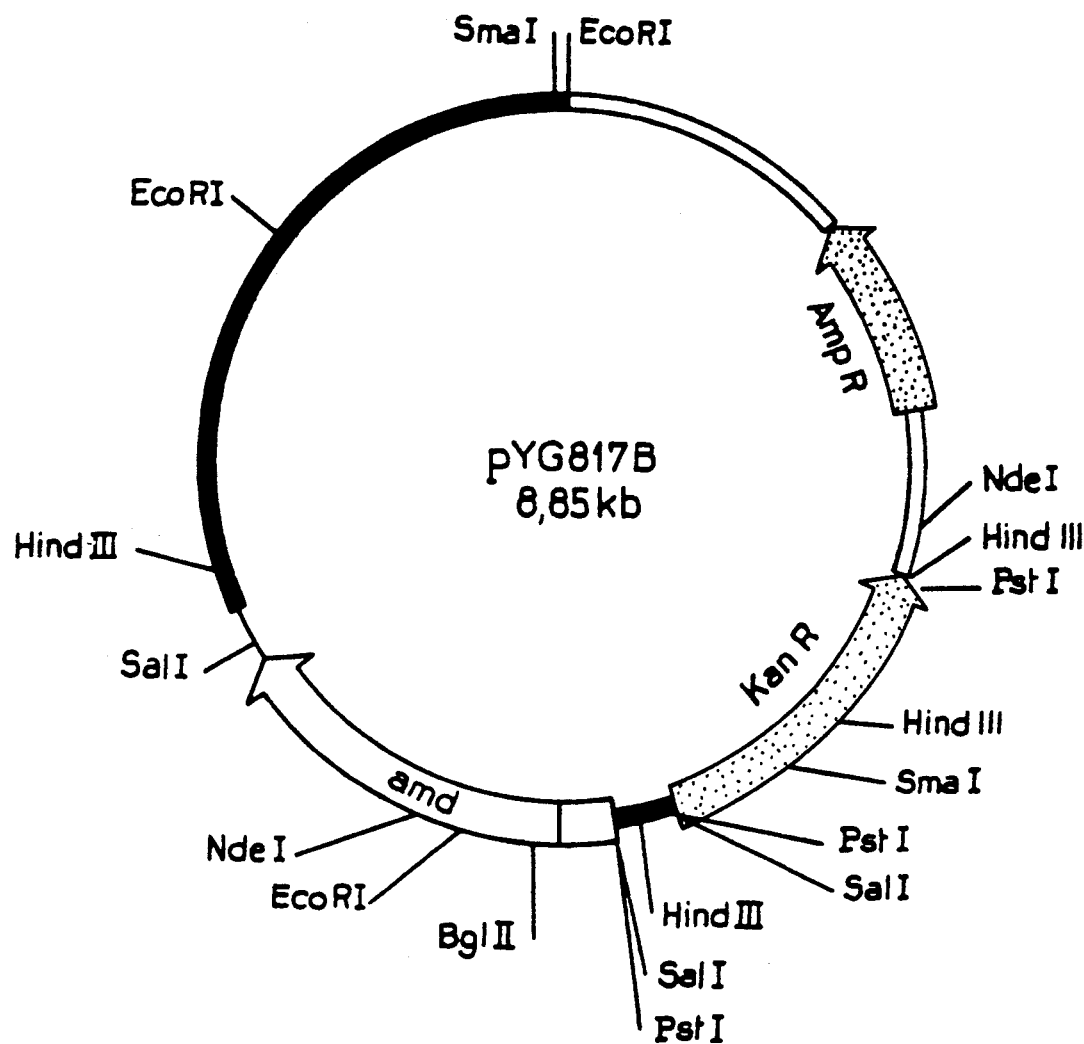
Figure 17:
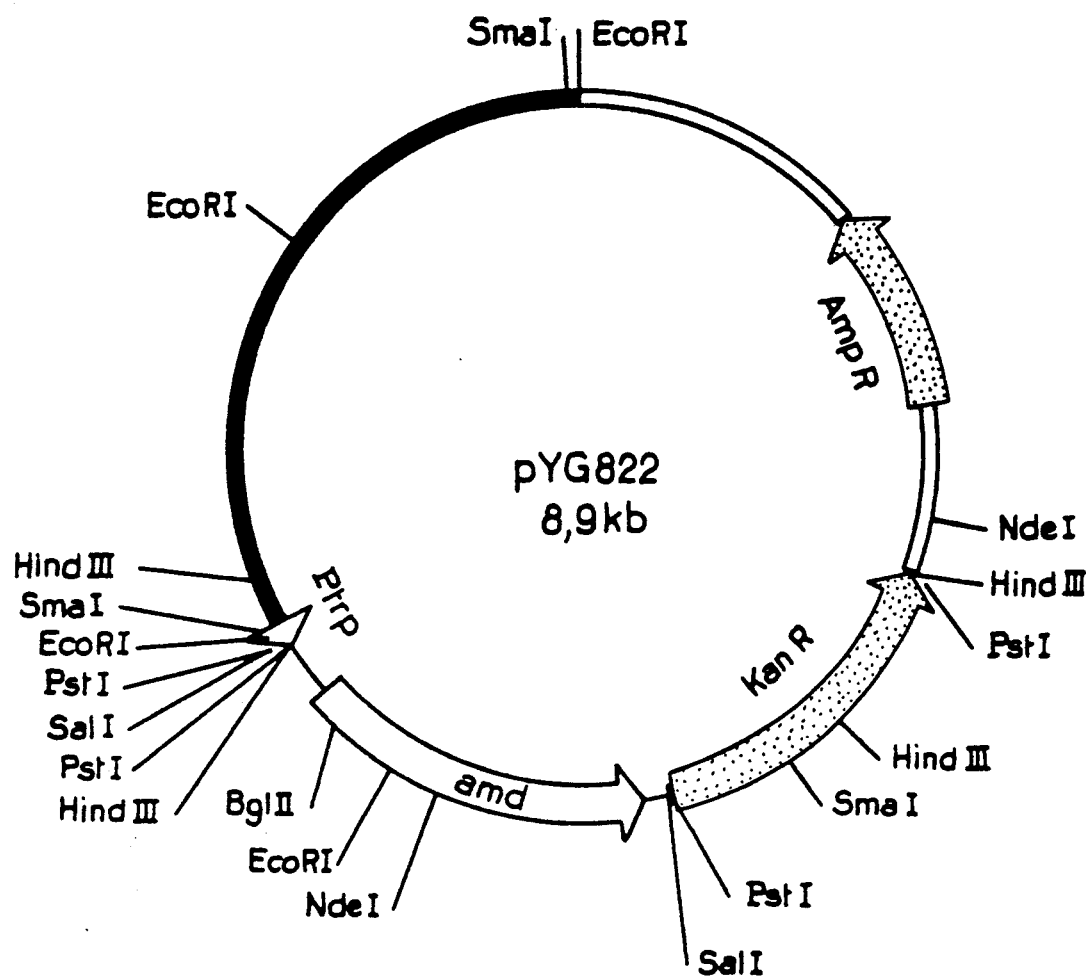

FIG. 13-1 and 13-2:
Nucleotide and peptide sequences of the enantioselective amidase gene of Rhodococcus (BamHI fragment from plasmid pXL1836).
FIG. 14:
Restriction map of shuttle vector pSV73.
FIG. 15:
Restriction map of expression plasmid pYG811B.
FIG. 16:
Restriction map of expression plasmid pYG817B.
FIG. 17:
Restriction map of expression plasmid pYG822.

STARTING PLASMIDS

Plasmid pXL1029 has been described in Jung et al. (1988), Ann. Inst. Pasteur/Microbiol. 139,129–146). It carries an EcoRI-NdeI fragment containing $P_R$cIts-RBScIIΔtRI.

EXAMPLE 1

Identification and purification of the enantioselective amidase of Brevibacterium R312

1.1. Identification (R,S)-2-(4-hydroxy-phenoxy)-propionamide (HPPAmide), a derivative of 2-aryloxy-propionamide, is a better substrate for the enantioselective amidase than 2-aryl-propionamide derivatives, notably 2-phenyl-propionamide and 2-(3-benzoyl-phenyl)-propionamide. Furthermore, the selectivity of the amidase vis-a-vis the R enantiomer of HPPAmide is representative of the selectivity vis-a-vis the S enantiomer of 2-aryl-propionamide derivatives.

As a consequence, the enantioselective enzymatic activity was detected using 2-(4-hydroxy-phenoxy)-propionamide as substrate. The reaction was carried out at 25° C. with agitation in a buffer of 50 mM sodium phosphate, pH 7.0, in the presence of Brevibacterium R312; it was stopped by addition of a mixture of 0.05M phosphoric acid, acetonitrile, and 1N HCl in a ratio of 55/40/5 (v/v). After centrifugation of the culture the supernatant was analyzed by reverse phase high performance liquid chromatography (HPLC) (Hibar-Merck RP-18, 5 μm). Elution was performed with a solution of 0.005M phosphoric acid and acetonitrile (85/15) (v/v). The respective concentrations of HPPAmide and HPPAcid were measured by comparing the elution peaks to a standard. For this substrate, the enantiomeric excess is defined as $(R-S)/(R+S) \times 100$ where R and S are the respective concentrations of the R and S enantiomers of HPPAcid. The enantiomeric excess was deduced either from polarimetric measurement (using the absorption of sodium at 589 nm), or by HPLC using a chiral column.

The activities obtained with whole cells and a soluble extract, respectively, were 15 U/mg and 24 U/mg of protein, (1 U=1 μmol HPPAcid formed per hour). The enantiomeric excess of (R)-HPPAcid is 95%. These results demonstrate that Brevibacterium R312 possesses an enantioselective amidase capable of hydrolyzing racemic 2-arylpropionamides to the corresponding S acids. This was verified by the hydrolyses of racemic 2-phenyl-propionamide and racemic 2-(3-benzoyl-phenyl)-propionamide to the respective corresponding S acids, with an enantiomeric excess higher than 93%.

1.2. Purification

The purification was carried out at 4° C. Cells (40 g dry weight Brevibacterium R312) were thawed and suspended in 300 ml Buffer A (50 mM sodium phosphate, pH 7, 5 mM β-mercaptoethanol). Cells were then broken by sonication and membrane debris were eliminated by centrifugation at 20000 rpm for 30 minutes. To 30 ml of supernatant, 25 ml of a 10% solution of streptomycin sulfate was added slowly, with stirring. After 45 minutes, the solution was clarified as above and the resulting supernatant was treated with ammonium sulfate. The protein fraction precipitating between 30.8% and 56.6% saturation of ammonium sulfate was collected by centrifugation and dissolved in 35 ml Buffer A, and then dialyzed slowly against the same buffer. The solution thus obtained was adjusted to 20% saturation of ammonium sulfate, centrifuged, then applied to a phenyl-Sepharose CL-4B column (Pharmacia) equilibrated with Buffer A at 20% saturation of ammonium sulfate. Active fractions were eluted with the same buffer, then concentrated by ultrafiltration to a volume of 18 ml using an Amicon Diaflo PM10 cell. Glycerol (10%) was then added to the concentrated solution, and the resulting solution was applied to an Ultrogel AcA 44 column (IBF-Biotechnics, France) previously equilibrated with 50 mM Tris-HCl, pH 7, 100 mM NaCl. Fractions containing the highest specific activity (approximately 32% of the total activity loaded onto the column) were collected, concentrated, and subjected to a supplementary filtration step on the same gel. In parallel, fractions containing the highest specific activity (approximately 30% of the total protein loaded onto the column) were analyzed by SDS-PAGE and stored. The enantioselectivity of the purified protein was also determined.

This purification method resulted in an enzyme more than 80% pure, with a specific activity of 815 U/mg. At this step, a major band of apparent molecular weight 59+/−5 KD which corresponds to at least 80% of the total proteins, is visible on SDS-PAGE. Moreover, the amidase activity eluted from an HPLC TSK 3000 column corresponds to a molecular weight of 122 KD, indicating that the enzyme is in a dimeric form.

Table 1 shows the characteristics of the different fractions. This table describes the different steps of the purification of the enantioselective amidase of Brevibacterium R312:

from 40 g of humid cells, after precipitation with streptomycin sulfate one unit (U) corresponds to 1 μmol HPPAcid formed per hour under the conditions described below.

TABLE 1

| Purification Step | Vol. (ml) | Quantity of protein (mg) | Activity (U/mg) | Yield % | Purification Factor |
| --- | --- | --- | --- | --- | --- |
| 1/ Crude extract | 325 | 1918 | 26.4 | 100 | 1 |
| 2/ Ammonium sulfate precipitate | 29.5 | 613 | 62.5 | 75 | 2.4 |
| 3/ Phenyl-sepharose eluate | 77 | 200 | 198 | 78 | 7.5 |
| 4/ AcA44, first eluate | 6 | 27 | 457 | 24.4 | 17.3 |
| 5/ AcA44, second eluate | 3 | 3.9 | 815 | 6.3 | 31 |

EXAMPLE 2

Cloning the enantioselective amidase of Brevibacterium R312

2.1. Derivation of protein sequences

The peptide sequences corresponding respectively to the N-terminal extremity (27 residues) and a tryptic internal fragment (21 residues) of the enantioselective amidase of Brevibacterium R312 were determined using the purified enzyme.

This was done by subjecting 3 nmol of the amidase preparation to reduction and carboxymethylation. The major protein component was then desalted, and purified to homogeneity by reverse phase HPLC. The N-terminal sequence was then determined by the Edman method of automatic sequential degradation, using an Applied Biosystems Model 470A instrument. The sequence presented in FIG. 1A was obtained in this manner. To obtain the additional internal sequence, the same quantity of protein was digested with trypsin. The reduced and carboxymethylated fragments were then separated by reverse phase HPLC (2.1×10 mm, flow 0.2 ml/min) using the following elution buffer: a gradient of 0 to 50% acetonitrile in 0.07% trifluoroacetic acid. The peptide eluting in a well-separated peak (at 40.8% acetonitrile) was sequenced (FIG. 1A).

2.2. Construction of the nucleotide probes

Two strategies were pursued.

In the first strategy, a 29-mer probe (59% minimal homology) was constructed, keeping in mind the codon usage in the tryptophan operon of *Brevibacterium lactofermentum* (7.7 kb sequence containing 6 cistrons: Matsui et. al., Mol. Gen. Genet. 209 p. 299, 1987), and using the sequence IDGALGSYDV of the internal fragment (presenting a smaller average degeneracy). The noncoding strand was synthesized with consideration of the relative thermodynamic neutrality of G:T pairing and by introducing several degeneracies in order to maximize the average theoretical frequency of codons considered (88% in relation to the usage of the chosen codons). These considerations led to a GC content in the probe of about 69%. The sequence of the probe (Sq 762) is shown in FIG. 1B.

In the second strategy, the PCR method described by Girgès et. al. (Nucleic Acids Res. 16, p. 10371, 1988) was used to obtain an exact nucleotide probe from a peptide corresponding to highly degenerated codons. To accomplish this, 25-mer oligonucleotides (see underlined sequences in FIG. 2A) were synthesized, corresponding to all the possibilities of coding of the first or last five codons of the N-terminal peptide sequence, and carrying EcoRI and HindIII sites respectively, at their 5' extremities. These 25-mers were used to prime an enzymatic amplification of Brevibacterium R312 genomic DNA. After 30 cycles of amplification the candidate fragment was purified on a gel, then inserted between the HindIII and EcoRI sites of bacteriophage M13mp19. In fact, two different hybridization temperatures of the primer (45° C. and (48° C.) were used, resulting in two candidate fragments. Thus after cloning the fragments, several clones from each temperature were sequenced and compared. The results are shown i FIG. 2A. It can be seen that apart from the degeneracies introduced by the primers, a DNA fragment (unique between primers) coding for the N-terminal extremity of amidase was well amplified. A 40-mer synthetic oligonucleotide (Sq 198) corresponding to this internal fragment was therefore used for the rest of the cloning as an exact probe for the N-terminal extremity of amidase.

FIG. 2B shows the nucleotide sequence of specific probe Sq 918.

The two probes Sq 762 and Sq 918 thereby obtained were labeled by 5' phosphorylation with $^{32}$P.

2.3. Cloning of the gene encoding the enantioselective amidase of Brevibacterium R312

The strategy consisted of first verifying the specificity of the probes and determining the nature of the genomic DNA fragment to be cloned by Southern blot. Briefly, Brevibacterium R312 genomic DNA was alternatively digest by several restriction enzymes corresponding to possible cloning sites, and in particular to sites present in the multisite cloning region of pUC plasmids. Notably, PstI was used. After electrophoresis through an agarose gel and transfer to a nylon membrane, the various digestions were hybridized to probes Sq 762 and Sq 918. The results shown in FIG. 3 demonstrate that the two probes present a sufficient specificity under the conditions of hybridization (at most one fragment hybridizing for each digestion). Furthermore, since the two probes give almost the same profile of hybridization, one might be led to believe that the hybridization signals of the sought-after gene are rather specific, and that the internal peptide obtained after tryptic digestion is very close to the N-terminal extremity. In particular, the hybridization footprints reveal the existence of a unique 5.4 kb PstI fragment that hybridized strongly with the two probes. It was therefore decided to clone this fragment.

For the cloning, all fragments of approximate size between 4.6 and 5.5 kb and 5.5 to 6.5 kb resulting from the PstI digestion of total genomic Brevibacterium R312 DNA, were purified on agarose, electroeluted, and ligated to pUC19 cut with PstI. After transformation of *E. coli* strain DH5α, 500 white colonies were obtained on X-gal medium, which theoretically correspond to recombinant microorganisms. Each colony was individually isolated, transferred onto a nylon membrane, then analyzed by hybridization with the $^{32}$P-labeled Sq 918 probe. Two clones hybridized very strongly; they were isolated and used in following steps.

Figure 4A:
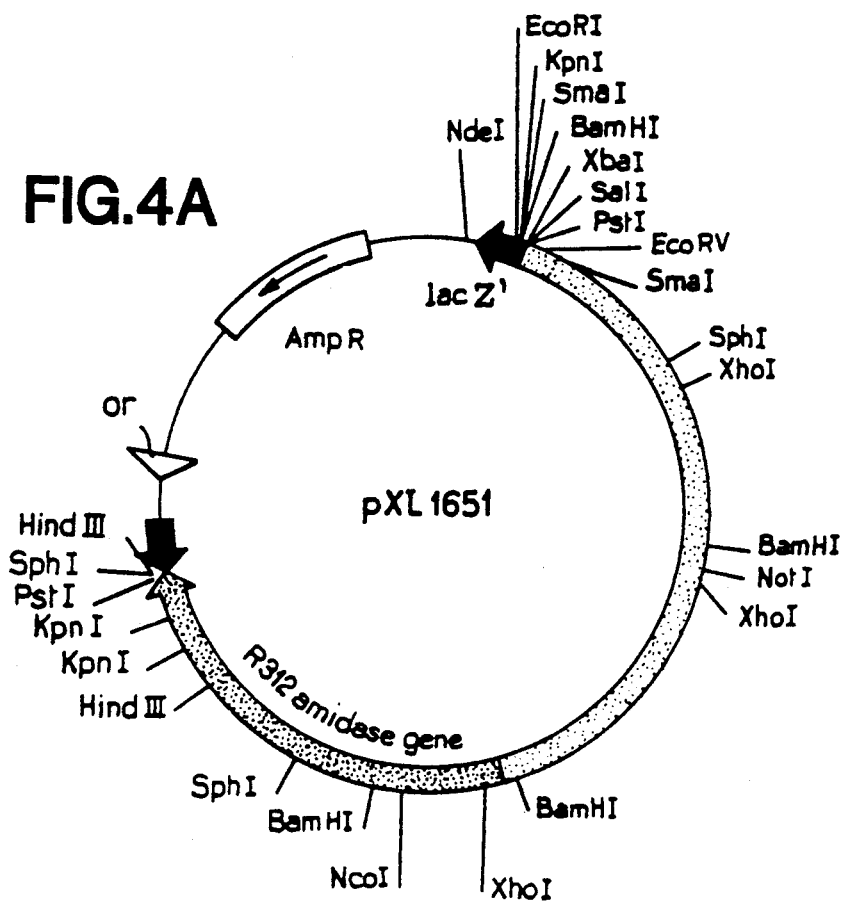
Figure 4B:
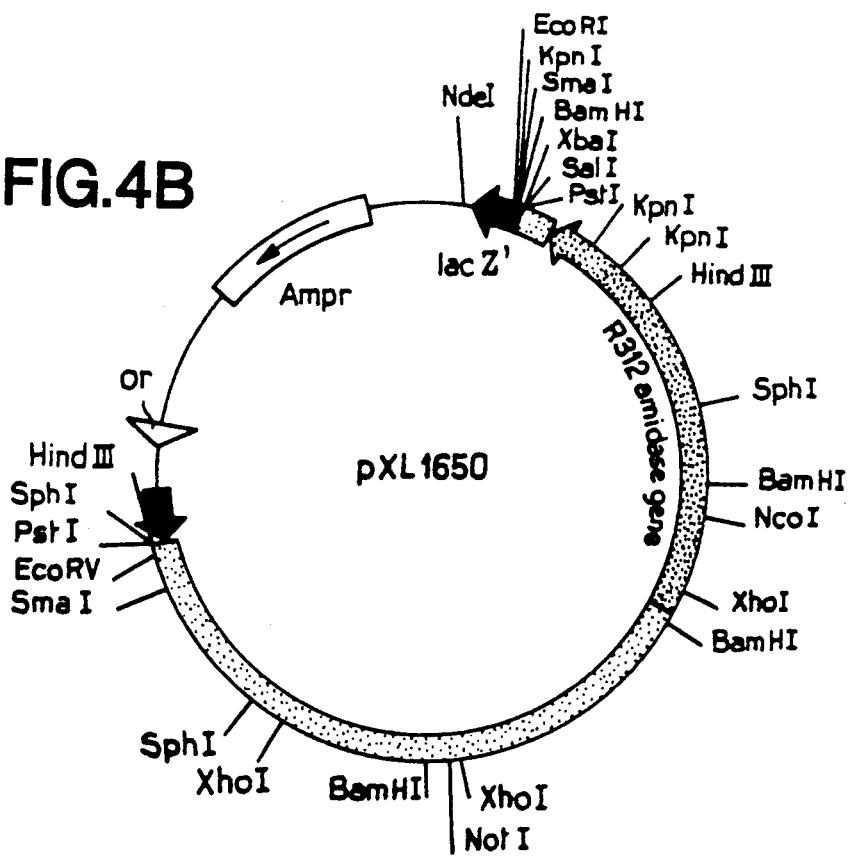
Figure 5:
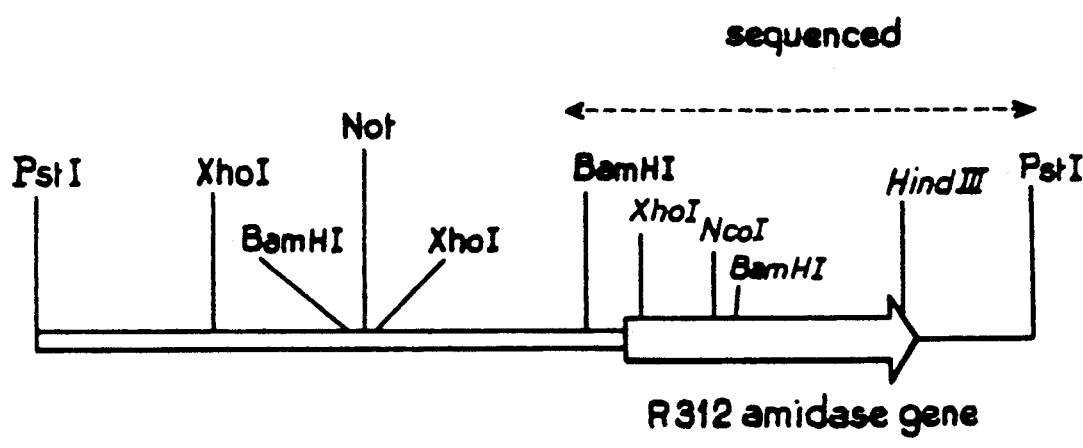

The two recombinant plasmids pXL1650 and pXL1651 isolated from these two clones were analyzed the probes as sequencing primers, and Southern blot. FIG. 4 shows that the two plasmids contain the same 5.4 kb PstI insert, in the two orientations. FIG. 5 shows the restriction map of this fragment. These two plasmids indeed contain the sequences coding for the characterized peptides, the tryptic fragment adjoining the N-terminal (FIG. 8). Furthermore, these results show that the gene coding for the enantioselective amidase of Brevibacterium R312 is located on a 2.3 kb BamHI-PstI fragment, oriented in the sense BamHI toward PstI. Given the position of the 5' extremity of the coding sequence and knowing that the enzyme is coded by at most 2 kb(57-63 KD monomer according to our estimations), it is certain that the entire gene was contained in the BamHI-PstI fragment that we therefore proceeded to sequence.

EXAMPLES 3

Sequence of the BamHI-PstI fragment containing the gene encoding the enantioselective amidase of Brevibacterium R312

Figure 6:
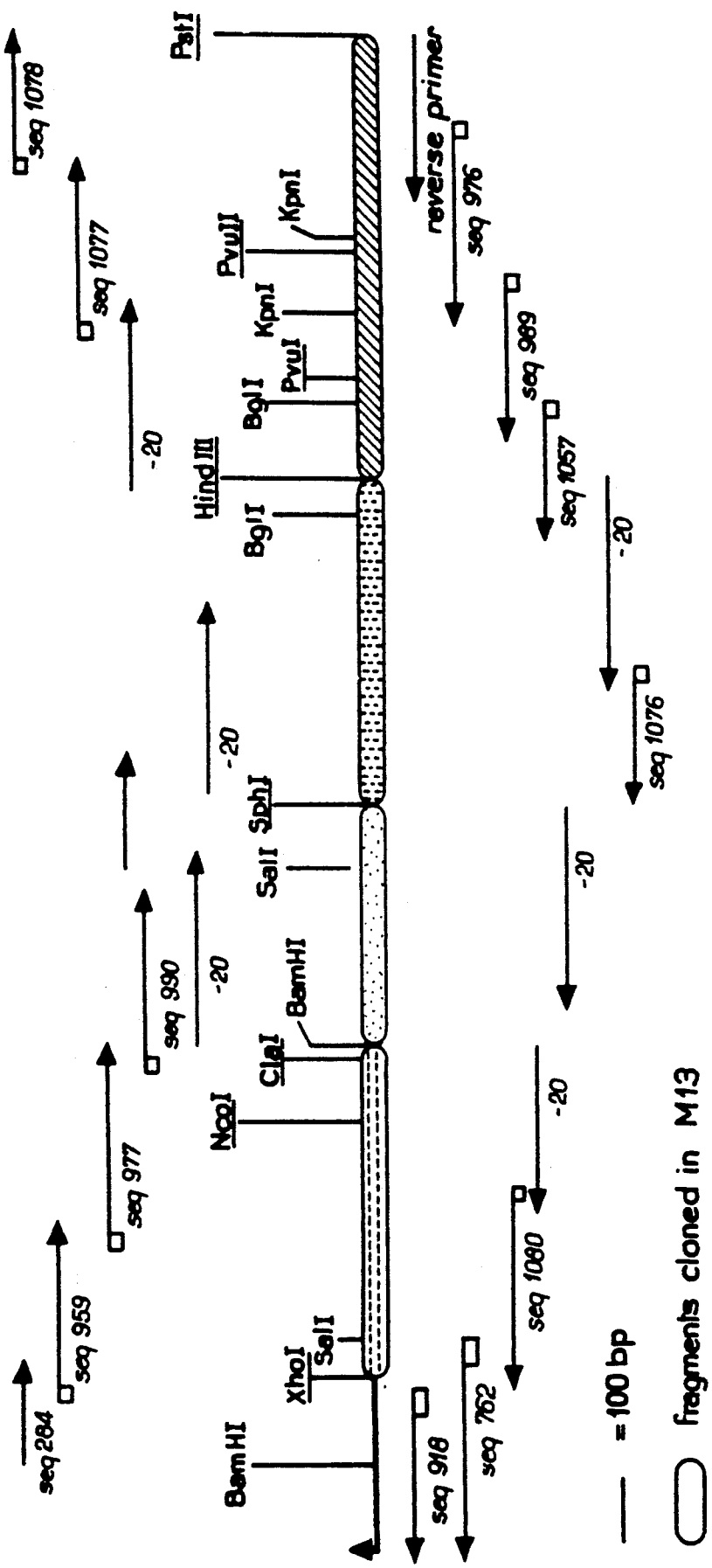
Figure 7:
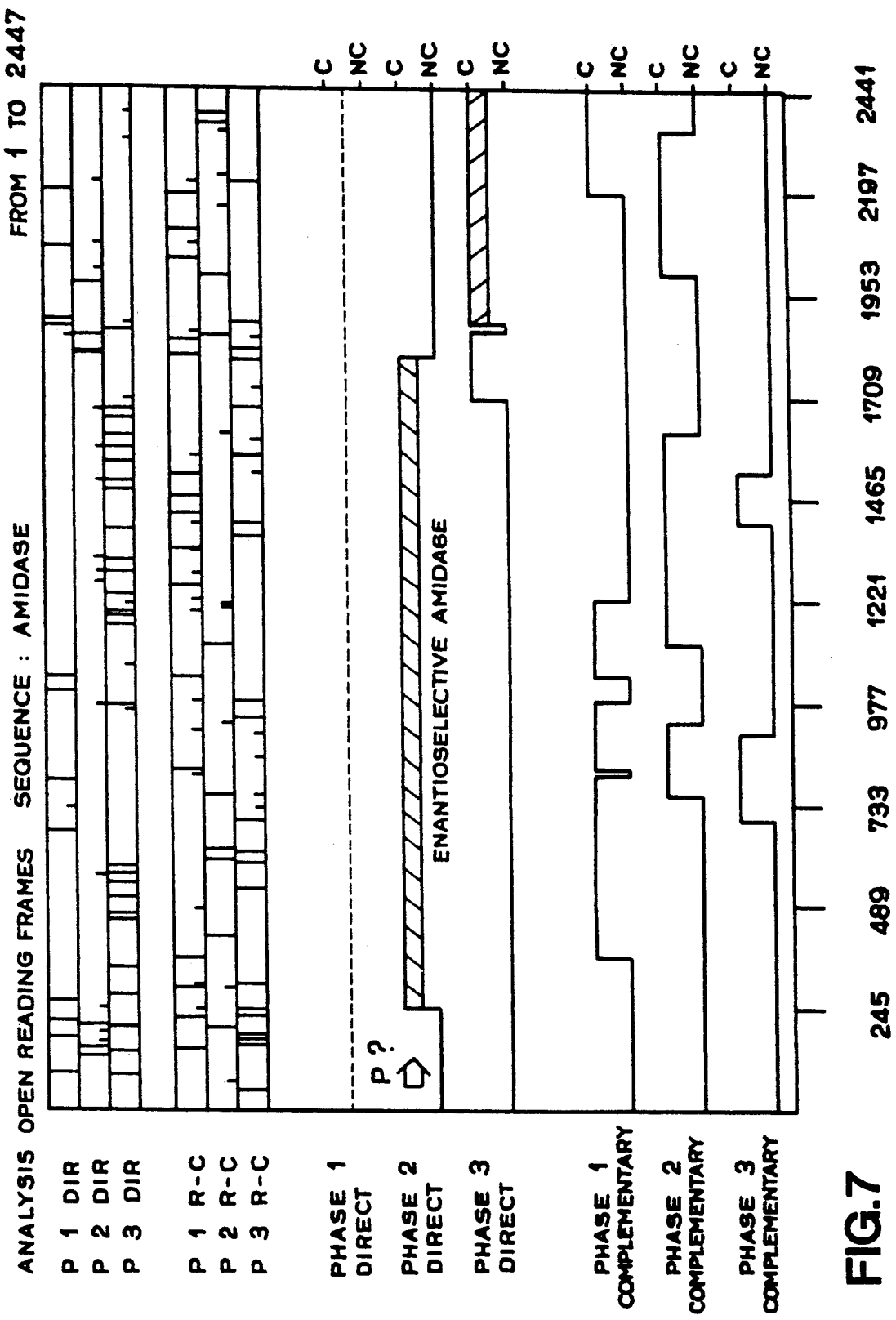

The sequencing strategy for the BamHI-PstI fragment is shown in FIG. 6. The various sequence were all obtained by the chain termination method (Sequenase kit in the presence of 7-deaza-dGTP; ($^{35}$S)-dATP either on single stranded M13 matrices carrying subfragments, or directly on plasmid pXL1650. To this end, several specific primers were also synthesized. The average GC content of the sequence obtained is 61.5%. FIG. 7 presents an analysis of the open reading frames; it is seen that the open reading frame corresponding to the amidase codes for 521 amino acids, a protein of calculated molecular weight of 54671. The GC content of this open reading frame is respectively 65.8%, 52.5% and 70% for the first, second and third codon positions, which is a typical distribution in coding sequences of GC-rich microorganisms. FIG. 8 shows the complete sequence of the BamHI-PstI fragment.

EXAMPLE 4

Expression in *E. coli* of the gene encoding the enantioselective amidase of Brevibacterium R312

4.1. Construction of plasmids

Several plasmids were constructed in which the structural gene of amidase, containing a homologous ribosome binding site (RBS) or the RBS from cII gene of lambda, was placed under the control of its own promoter, the promoter of the tryptophan operon, or the right temperature sensitive promoter of lambda. Plasmid pXL1650 (FIG. 4) was obtained by insertion of the 5.4 kb fragment resulting from the PstI digestion of total Brevibacterium R312 genomic DNA, into the unique PstI site of plasmid pUC19. This plasmid therefore carries the promoter of the lactose operon Plac, followed by a ribosome binding site and the structural gene encoding the enantioselective amidase of Brevibacterium R312, as well as a marker encoding ampicillin resistance.

Figure 9:
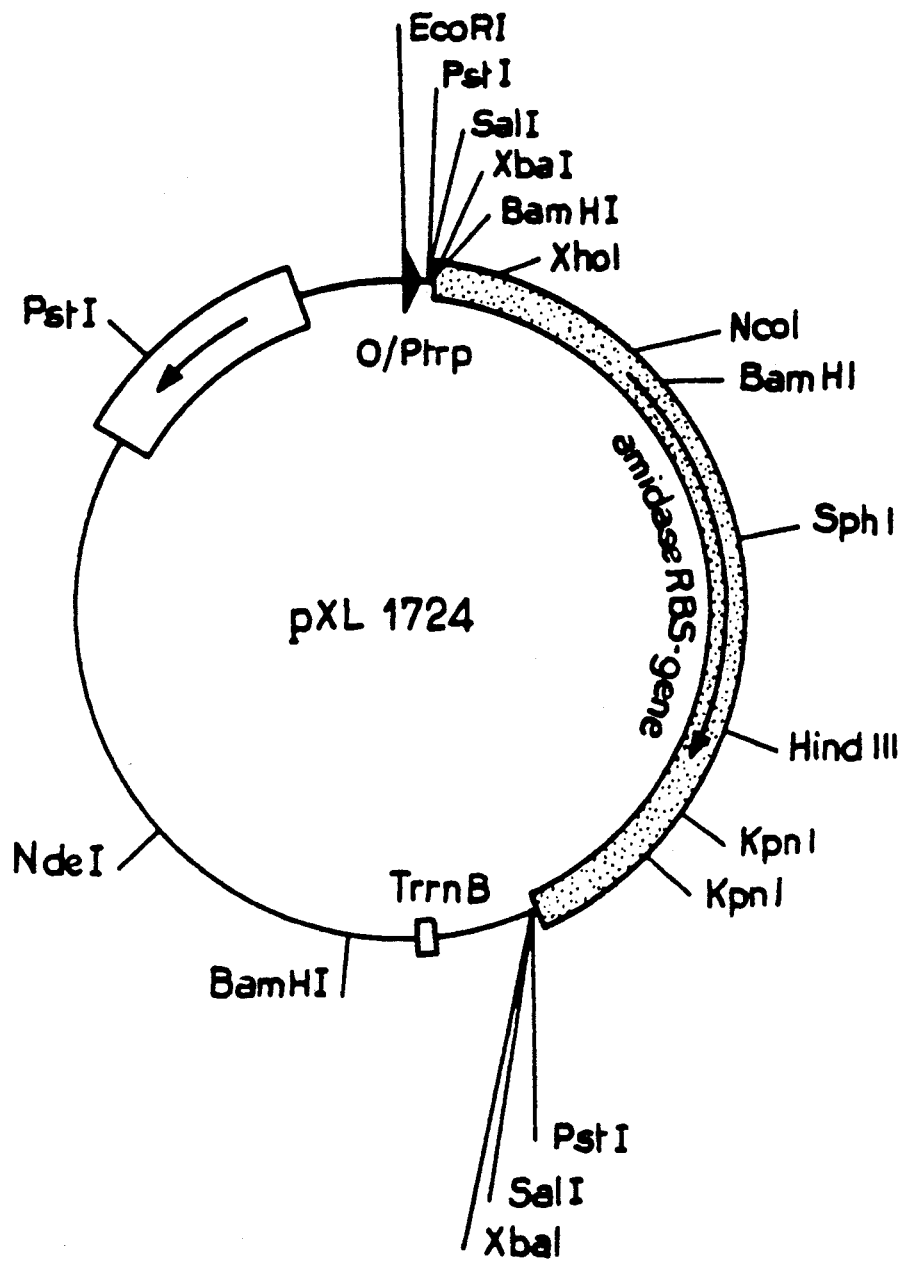

Plasmid pXL1724 (FIG. 9) contains the 2.3 kb BamHI-PstI fragment excised from the 5.4 kb PstI fragment under control of the promoter of the tryptophan operon of *E. coli*. In this construct, the amidase gene of Brevibacterium R312 is therefore preceded by 58 base pairs upstream of the ATG codon containing its own ribosome binding site (FIG. 8).

Two other constructions were made in which the structural gene encoding the enantioselective amidase of Brevibacterium R312 was placed under the control of heterologous promoters, with heterologous ribosome binding sites. These plasmids (pXL1751 and pXL1752) were obtained as follows:

Plasmid pXL1724 was mutagenized by PCR in order to substitute an NdeI site (CATATG) for the ATG codon situated upstream of the amidase structural gene. Amplification was carried out using a primer corresponding to the NdeI site hybridizing with initiation ATG codon, and a primer corresponding to an XhoI site situated downstream of the ATG codon. The amplified fragment was then excised by digestion with NdeI and XhoI.

Utilization of promoter Ptrp:

Into plasmid pXL1724 digested by EcoRI and XhoI, was inserted an EcoRI-NdeI fragment carrying the Ptrp promoter and the ribosome binding site of the lambda cII gene in which the termination sequence tR$_1$ has been deleted, and the 5' region of the amidase structural gene (fragment NdeI-XhoI). This generated plasmid pXL1751 (FIG. 10).

Utilization of promoter P$_R$cIts:

The same strategy was employed, this time by using the EcoRI-NdeI fragment from plasmid pXL1029 containing the P$_R$cIts promoter and the ribosome binding site of the lambda cII gene deleted of the termination sequence tR$_1$. This generated plasmid pXL1752 (FIG. 11).

4.2. Expression of the amidase gene of Brevibacterium R312 in *E. coli* B and *E. coli* K12 E103S LPlasmids pXL1751 and pXL1752 were used to transform strains *E. coli* B, and *E. coli* K12 E103S, respectively, by the calcium chloride method. Selection of recombinant microorganisms was carried out in ampicillin medium.

The expression of the enantioselective amidase of Brevibacterium R312 was measured after sonication of the cells, by SDS-PAGE of the crude fractions or, after centrifugation, of the pellet and supernatant. The results in FIG. 12 show a high level of amidase expression, representing up to 20% of total protein.

EXAMPLE 5

Utilization of the enantioselective amidase of Brevibacterium R312 for the enantioselective synthesis of 2-aryl-propionic acids The following strains were used in that which follows:

*E. coli* (pXL1751)—the amidase coding sequence is placed under the control of the promoter of the tryptophan operon.

*E. coli* (pXL1752)—amidase is produced by raising the temperature from 30° C. to 42° C. at the end of the exponential phase (P$_R$ promoter of lambda under control of the temperature sensitive repressor cIts).

Two control strains were also used:

*E. coli* (pXL906)— equivalent to *E. coli* (pXL1751) with the amidase gene replaced by the gene IL1$\beta$.

*E. coli* (pXL1029)— equivalent to *E. coli* (pXL1752) with the amidase gene replaced by the gene IL1$\beta$.

The following procedure was used to test the activity of these microorganisms:

A cell suspension grown under appropriate inducing conditions was added to a solution containing:
  hydroxy-4-phenoxy-2-propionamide (HPPAm), or
  phenyl-2-propionamide (PPAm), or
  the amide of ketoprofen (KAm), for example.

The reaction mixture was then diluted in a buffer containing acetonitrile:N hydrochloric acid (90:10) (v/v), and the cells were eliminated by centrifugation. The reaction mixture was resolved by HPLC and the amidase activity was calculated. The results shown in Table 2 demonstrate the efficiency of this system.

Table 2 shows the specific activity of the amidase of Brevibacterium R312, as produced in *E. coli* in inducing conditions, toward the racemic substrates HPPAm, PPAm and KAm, as well as the enantiomeric excess of the chiral acids produced. In this experiment, *E. coli* strains harboring plasmids pXL1751 (amidase) or pXL906 (control) were grown at 37° C.

TABLE 2

| E. coli strains in inducing conditions | Specific activity µmol/h/g protein | | | Enantiomeric excess % | | |
|---|---|---|---|---|---|---|
| | HPPAm | PPAm | KAm | HPPA R+ | PPA S+ | Keto S+ |
| pXL 1751 | 1300 | 50 | 4 | 93 | 96 | 95 |
| pXL 1752 | 1300 | 50 | 5 | 94 | 97 | 95 |
| pXL 906 | 0 | nd | nd | nd | nd | nd |
| pXL 1029 | 14 | 0 | 0 | nd | nd | nd |

Table 3 shows the specific activity of the amidase of Brevibacterium R312 (expression plasmid pXL1751), as produced in *E. coli* grown at 28° C. in induced or repressed conditions, toward the racemic substrates KAm, as well as the enantiomeric excess of the chiral acid produced.

TABLE 3

| Bacterial strain | Plasmid | Repressor (1) | Specific activity µmol/h/g protein | ee (%) |
|---|---|---|---|---|
| E. coli | pXL1751 | — | 55 | 96 |
| " | " | Trp | 13 | nd | nd = not determined.
ee: enantiomeric excess (%).
Note (1) = Trp: L-tryptophane.

Therefore, *E. coli* strains harboring the amidase gene of Brevibacterium R312 (genotype Amd+) can efficiently hydrolyze the following three amides (phenotype AMD+):
  2-(4-hydroxy-phenoxy)-propionamide (HPPAm)
  2-phenyl-propionamide (PPAm)
  amide of ketoprofen (KAm).
The enantiomeric excess obtained was always greater than 93%.

EXAMPLE 6

Purification of the enantioselective amidase of Rhodococcus

I. Assay of enzymatic activity

The active fraction was incubated at 30° C. for 30 minutes in 500 µl of buffer (0.1M Tris HCl pH 7.5, 5 mM DTT, 18 mM 2-phenylpropionamide). After incubation, 2 ml of a mixture of acetonitrile/HCl 1N (90/10) and then 2 ml of a mixture of 50 mM $H_3PO_4/CH_3CN$ (75/25) were added to the reaction mixture. After centrifugation at 5000 rpm for 10 minutes, an aliquot of the supernatant was subjected to HPLC to measure the reaction products.
  Column:Nucleosil 5-C18 25 cm
  Eluant:50 mM $H_3PO_4/CH_3CN$ (75/25)
  Loading:10 µl
  Flow rate:1 ml/min.

A unit of activity is defined as the quantity of enzyme necessary for the hydrolysis of 1 µmol 2-phenyl-propionamide per hour.

II. Purification protocol 6.1. Preparation of the enzyme extract 7 g of cells were suspended in 15 ml 0.1M Tris HCl pH 7.5, 5 mM DTT, and sonicated for 15 minutes at 4° C. The crude enzyme extract was collected by centrifugation at 50000 rpm for 1 hour.

6.2. First ion-exchange chromatography

To 20 ml of crude extract, 20 ml of Buffer A (25 mM Tris HCl pH 7.5, 5 mM DTT) was added. The sample was injected onto a Mono Q HR 10/10 column (Pharmacia) equilibrated in Buffer A, at a flow rate of 3 ml/min. After washing the column, the proteins were eluted with a linear 1 hour gradient of 0.1 to 1M KCl at a flow rate of 3 ml/min. Fraction size was 6 ml. The amidase eluted in 18 ml at approximately 0.3 M KCl.

6.3. Second ion-exchange chromatography

The active fraction were combined and concentrated to 2 ml using a Centriprep ultrafiltration system (Amicon). After dilution with 6 ml Buffer A, 4 ml of the sample was injected at 1 ml/min onto a Mono Q HR 5/5 column equilibrated in Buffer A. Proteins were eluted with a linear gradient of 0 to 0.5M KCl in Buffer A. Active fractions were combined and adjusted to 15% glycerol (v/v), then concentrated to 1 ml as above.

6.4. Hydrophobic chromatography 1 ml of Buffer B (0.1M Tris HCl pH 7.5, 0.5 mM DTT, 1.7M $(NH_4)_2SO_4$) was added to the sample which was then injected (in two injections) onto a Phenyl-Separose HR 5/5 column (Pharmacia) at a flow rate of 0.25 ml/min. Proteins were eluted at 0.5 ml/min with a decreasing linear gradient of $(NH_4)_2SO_4$ (1.7M to 0M) in 25 ml. Fraction size was 0.5 ml. Active fractions were adjusted to 15% glycerol then diluted to 1 ml with Buffer A.

6.5. Hydroxyapatite chromatography

The sample was injected at 0.5 ml/min onto a Bio-Gel HPHT column (Bio-Rad) equilibrated with Buffer C (85 mM Tris HCl pH 7.5, 0.5 mM DTT, 10 µM $CaCl_2$, 15% glycerol). The amidase was eluted at a flow rate of 0.5 ml/min with a linear gradient of 0 to 100% of buffer 0.35M potassium phosphate pH 7.5, 0.5 mM DTT, 10 µM $CaCl_2$, 15% glycerol in Buffer C, in 20 minutes.

These steps allow the purification to homogeneity of an enzyme with a specific activity of 988 U/mg of protein.

The enzyme thereby obtained is present in the form of a dimer of identical subunits of apparent molecular weight 53+/−2 KD.

EXAMPLE 7

Cloning of the gene encoding this amidase

After a supplementary purification step on TSK-G3000 SW, the enzyme was subjected to sequencing. The N-terminal extremity was inaccessible to Edman-type chemistry, and so a total trypsin hydrolysis was carried out and three HPLC fractions of the hydrolysate—123, 124 and 162—provided peptides that allowed an unambiguous sequence to be obtained. From the sequence obtained from fraction 123, a 32-mer nucleotide probe was synthesized, corresponding to a mixture of 8 oligonucleotides and containing 7 inosines in positions degenerated at least three times:

Probe A (from peptide 123)
A T V D V P V P D Y A
5'                                                    3'
GCIACIGTIGATGTICCIGTICCIGATTATGC
            C                              C       C The efficiency of this probe, labeled at the 5' end with $^{32}P$, was tested by Southern transfer onto genomic DNA from Rhodococcus previously digested by one of the following restriction enzymes: SstI, SphI, SmaI, PstI, KpnI, EcoRI, SalI and BamHI. Experimental conditions were as follows: hybridization buffer, 5×SSC, 5×Denhardt, 0.1% SDS, 50 mM NaPO₄ pH 6.5, 250 μg/ml salmon sperm DNA; hybridization temperatures were 50° C. or 55° C. (two experiments); wash conditions were 1 hour in 6×SSC at room temperature and 5 min. in 2×SSC, 0.1% SDS at 50° C.

Under these conditions, probe A gave strong, unambiguous signals; in particular, with the BamHI, KpnI, SphI, SstI, SmaI, SalI and PstI digestions, a single genomic band was found, strongly hybridizing to probe A. For PstI digestion, the size of the hybridizing signal to probe A corresponds to a genomic fragment of approximately 3.2 kb.

The 3 to 4 kb PstI digestion fragments of genomic DNA were thus purified by preparative electrophoresis through agarose followed by electroelution, then ligated to plasmid pUC19 that had been cut by PstI. After transformation of *E. coli* strain DH5α, 600 clones that were white on LB Amp-X-gal were repicked individually and probed with probe A by colony hybridization, in stringency conditions similar to the Southern. The 9 clones with particularly strong hybridization signals were then analyzed by restriction of plasmid DNA. Among 6 of these clones having clearly inserted the same 3.2 kb fragment in the two orientations, 2 clones representing each orientation (pXL1835 and pXL1836) were analyzed in more detail (detailed mapping, Southern analysis), thereby confirming that the desired fragment had been obtained.

EXAMPLE 8

Sequence of the 3.2 kb PstI fragment

The complete nucleotide sequence of the 3.2 kb PstI fragment was determined for the two strands. The GC content of this fragment was 62.4%, similar to the GC content of R312 (approximately 62%). Analysis of the sequence revealed an open reading frame of 1386 nucleotides (position 210 to 1595) coding for a polypeptide of 462 amino acids (calculated molecular weight of 48554) that contained the three peptide previously obtained by sequencing the trypsic fragments. This open reading frame is included in a BamHI subcloned fragment whose nucleotide sequence is shown in FIG. 13.

The 3 underlined peptide sequences correspond to the peptide fragments determined directly on the trypsic fragments of the purified enzyme (peptide 123, 124 and 162). The underlined nucleotide sequence corresponds to the (degenerated) probe used to clone the gene. The peptide sequence in italics corresponds to residues 137 to 193 that are highly conserved between the enantioselective amidases of Brevibacterium strain R312 and the strain of the genus Rhodococcus (see below).

This open reading frame represents the structural gene of the enantioselective amidase.

EXAMPLE 9

Homologies between different amidases: identification of a sequence characteristic of amidase activity A comparison of the peptide sequences of the enantioselective amidase of R312 (FIG. 8) and the amidase shown in FIG. 13 shows a strong homology in about two-thirds of the sequence, between residues 150 and 300 of R312 (50% strict identity), with the homology reaching 67% between residues 159 and 215.

A search of the GENPRO gene bank for homologous sequences revealed some strong homologies between the 150 to 200 region, and the sequences of the acetamidase of *Aspergillus nidulans*, the indolacetamide hydrolases (IAH) of *Pseudomonas syringae* and *Bradyrhizobium japonicum*, the tms2 protein of *Agrobacterium tumefaciens*, and the 6-aminohexanoate-cyclic-dimerhydrolyases (ACDH) of Flavobacterium strain K172 and Pseudomonas strain NK87.

Table 4 shows the homology of peptide 137-193 of the amidase described above, with the respective sites of these other enzymes (expressed as % strict identity of amino acids):

TABLE 4

| Amidase | % homology |
|---|---|
| R312 | 65.5 |
| tms2 *A. tumefaciens* | 64.3 |
| LAH *P. syringae* | 61.8 |
| ACDH (F.K172 or P.NK87) | 61.4 |
| IAH *B. japanicum* | 54.4 |
| Acetamidase (*A. nidulans*) | 47.4 |

This strongly conserved region is most likely responsible for the activity of these enzymes (catalytic site).

EXAMPLE 10

Expression of the enantioselective amidase in *E. coli*

In order to confirm the identification of the phase coding for the enantioselective amidase, an NdeI site (CATATG) was created by PCR at the presumed ATG codon at position 210 (FIG. 13), and the fragment between this site and the SalI site at position 1683, containing uniquely the region coding for amidase, was placed under the control of signals functional in *E. coli* for transcription initiation (promoters Ptrp or P$_R$) and translation (ribosome binding site cII). The vectors thereby obtained (pXL1893, Ptrp; and pXL1894, P$_R$-cIts) are similar to vectors pXL1752 and pXL1751 expressing the amidase of R312, as previously described. Expression from plasmids pXL1893 and pXL1894 was studied in *E. coli* B and *E. coli* K12 E103S, respectively. A protein comigrating with the purified amidase was produced specifically at 42° C. in the presence of plasmid pXL1894.

EXAMPLE 11

Expression of the enantioselective amidase in corynebacteria

1. Construction of the expression vectors

These vectors are derived from replicating vectors for corynebacteria. They include
  a replicon of *E. coli*
  a replicon of corynebacteria
  a selectable marker
  an Amd sequence.

Vector pSV73 (FIG. 14): this plasmid is derived from plasmid pSR1 of *C. glutamicum* (Yoshihama et. al., J. Bacteriol. 162, 591, 1985) by insertion of plasmid pUC8 containing an *E. coli* replicon and the kanamycin resistance gene carried on transposon Tn903.

This plasmid was used to construct the different expression vectors for the Amd sequences shown in FIG. 13, notably:

Vectors pYG811A and B (FIG. 15). These expression vectors are obtained by cloning the Amd sequence contained in the SalI fragment represented in FIG. 13 into the SalI site of pSV73, in both orientations.

Vectors pYG817A and B (FIG. 16). These expression vectors are obtained by cloning the Amd sequence contained in the BamHI fragment represented in FIG. 13, into the BglII site of pSV73, in both orientations.

Vector pYG822 (FIG. 17). This expression vector is derived from pSV73 by inserting between the SalI and BglII sites an expression cassette containing the Amd sequence shown in FIG. 13 under control of the Ptrp promoter of the tryptophan operon of *E. coli*.

Other cryptic corynebacterium plasmids can be used for the construction of expression vectors for the Amd sequence that are functional in corynebacteria. For example, plasmid pX18, isolated from *B. lactofermentum* (Yeh et. al., Gene, 47 301–306, 1986), allowed the construction of shuttle vectors pYG820A and pYG820B which can replicate in Brevibacterium R312 and therefore can be used as recipients for cloning and expression experiments in several corynebacteria.

2. Transformation of corynebacteria

All known transformation techniques can be used, and notably the protoplast-regeneration technique described by Yoshima et. al. cited above. However the applicants have shown that the electroporation technique is very efficient, augmenting the frequency of transformation up to 1000-fold.

SDS-PAGE analysis of sonicated cells is used to investigate the intracellular expression of the enzyme in the recombinant hosts.

EXAMPLE 12

Enzymatic catalysis

This example illustrates the usage of Amd-type proteins, or the recombinant microorganisms expressing these proteins, for the enantioselective synthesis of optically active organic acids by hydrolysis of the corresponding racemic amides.

1. Preparation of the cells

The different strains were cultured in 2 liter Erlenmeyer flasks in 600 ml medium, at 28° C. in appropriate culture conditions with an agitation of 150 turns/min. After termination of the culture, cells were harvested, washed in a solution of NaCl (9 g/l) and stored at −18° C.

2. 2-phenyl-propionamide as substrate

The protocol is as follows:

The 2-phenyl-propionamide and the cell suspension were added to a flask equipped with a stirrer, and the volume was adjusted to 5 ml with 50 mM potassium phosphate buffer pH 7.0. The flask was placed in a thermostated crystallizing dish at 25° C. with stirring for 1 hour. The reaction mixture was then diluted with a solution of acetonitrile/HCl (9/1), (v/v), and bacteria and cell debris were eliminated by centrifugation. The composition in acid and amide was determined by HPLC.

The results obtained in Brevibacterium R312 and *Brevibacterium lactofermentum* (ATCC 21086) are as follows:

TABLE 5

| Strain | Plasmid | Specific activity μmol/h/mg protein |
|---|---|---|
| Brevibacterium R312 | pSV73 | 0.1 |
| " | pYG811A | 4.3 |
| " | pYG811B | 5.4 |
| *B. lactofermentum* | pSV73 | 0 |
| " | pYG822 | 2.8 |

3. Racemic ketoprofen amide as substrate

As shown in Table 6, it is seen that recombinant corynebacteria expressing the amidase from Rhodococcus gave significantly higher activities than from control cells transformed with pSV73.

TABLE 6

| Bacterial strain | Plasmid | Inducer | Specific activity μmol/h/mg protein | (%) |
|---|---|---|---|---|
| Brevibact. R312 | pSV73 | IBN | 0.01 | nd |
| " | pYG811A | IBN | 0.04 | 96 |
| " | pYG811B | IBN | 0.04 | 94 |
| *B. lactofermentum* | pSV73 | IBN + IBNAm | 0 | nd |
| " | pYG822 | IBN + IBNAm | 0.02 | nd | nd = not determined.
ee: enantiomeric excess (S + ketoprofen).
Note (1) = IBN: isobutyronitrile; IBNAm: isobutyramide.

---

We claim:

1. An isolated DNA segment consisting essentially of a DNA segment encoding a polypeptide having enantioselective amidase activity wherein said DNA segment is selected from the group consisting of
   (a) a segment encoding the enantioselective amidase of Brevibacterium R312, with a nucleotide sequence of SEQ ID NO:1, as shown in FIG. 8;
   (b) a segment encoding the enantioselective amidase of Rhodococcus, with a nucleotide sequence of SEQ ID NO:3, as shown in FIG. 13;
   (c) an analog of the segment of (a) or (b), wherein said analog encodes the enantioselective amidase of (a) or (b), and wherein said analog differs from the nucleotide sequence of (a) or (b) due to the degeneracy of the genetic code; and
   (d) DNA which hybridizes with the segment of (a), (b) or (c), or with a fragment thereof, wherein said DNA segment encodes a polypeptide having enantioselective amidase activity.

2. The DNA segment of claim 1, wherein said DNA segment comprises a segment selected from the group consisting of
   (a) a segment encoding amino acids 137 to 193 of SEQ ID NO: 2 and FIG. 13;
   (b) a segment encoding amino acids 159 to 215 of SEQ ID NO: 4 and FIG. 8; and
   (c) a segment encoding an amino acid sequence having at least 50% homology with the amino acid sequence of (a) or (b).

3. An isolated and purified DNA segment selected from the group consisting of a DNA segment consisting essentially of the coding region of the sequence of SEQ ID NO: 1 FIG. 8, and a DNA segment consisting essentially of the coding region of the sequence of SEQ ID NO: 3 FIG. 13, wherein said coding region encodes a polypeptide consisting essentially of an enantioselective amidase.

4. An isolated gene, wherein said gene comprises the DNA segment of any one of claims 1 and 2 and further comprises native regulatory DNA sequence elements associated with a polypeptide coding region of the DNA segment.

5. A transformed microorganism comprising an expression cassette, wherein said expression cassette comprises the isolated and purified DNA segment of any one of claims 1 and 3 under the control of at least one regulatory DNA sequence allowing the expression of said isolated and purified DNA segment in said microorganism.

6. The microorganism of claim 5, wherein said regulatory DNA sequences allowing the expression of said isolated and purified DNA segment are selected from the group consisting of a transcription initiation site and a translation initiation site.

7. The microorganism of claim 6, wherein said transcription initiation site comprises a promoter region and said translation initiation site comprises a ribosome binding site.

8. The microorganism of claim 7, wherein said promoter sequence is selected from the group consisting of a promoter sequence homologous to said polypeptide, and a promoter sequence heterologous to said polypeptide.

9. The microorganism of claim 7, wherein said ribosome binding site is selected from the group consisting of a ribosome binding site homologous to said polypeptide, and a ribosome binding site heterologous to said polypeptide.

10. The microorganism of claim 7, wherein said promoter sequence is selected from the group consisting of
the strong promoters of corynebacterium phages;
the Ptrp promoter of the tryptophan operon;
the Plac promoter of the lac operon;
the left promoter $P_L$ of phage lambda; and
the right promoter $P_R$ of phage lambda.

11. The microorganism of claim 10, wherein said promoter sequence is selected from the group consisting of
the Ptrp promoter of the tryptophan operon; and
the right promoter $P_R$cIts of the phage lambda.

12. The microorganism of claim 7, wherein said ribosome binding site is derived from the cII gene of phage lambda.

13. The microorganism of claim 5, wherein said expression cassette further comprises a gene conferring on said microorganism a means of selection.

14. The microorganism of claim 13, wherein said means of selection is a selectable marker conferring resistance to an antibiotic.

15. The microorganism of claim 5, wherein said expression cassette comprises the Ptrp promoter of the tryptophan operon, the ribosome binding site of the cII gene of phage lambda deleted of the transcription termination sequence tR1, the DNA encoding the enantioselective amidase gene of Brevibacterium R312, and a gene conferring ampicillin resistance on said microorganism.

16. The microorganism of claim 5, wherein said expression cassette comprises the temperature sensitive right promoter of phage lambda $P_R$cIts, the ribosome binding site of the cII gene of phage lambda deleted of the transcription termination sequence tR1, the DNA encoding the enantioselective amidase gene of Brevibacterium R312, and a gene conferring ampicillin resistance on said microorganism.

17. The microorganism of claim 5, wherein said microorganism is selected from the group consisting of *E. coli*, Brevibacterium, Corynebacterium, and Rhodococcus.

18. The microorganism of claim 17, wherein said microorganism is selected from the group consisting of *E. coli* B and *E. coli* K12 E103S.

19. A method for preparing an enantioselective amidase, wherein said method comprises
cultivation of the microorganism of claim 5 under conditions which allow the expression of the DNA segment encoding said enantioselective amidase;
separation of said microorganism; and
extraction of said enantioselective amidase.

20. The method of claim 19, wherein said culture is sonicated, fractionated with ammonium sulfate, chromatographed on phenyl-Sepharose, and subjected to filtration using an Ultrogel AcA 44 column.

* * * * *

UNITED STATES PATENT AND TRADEMARK OFFICE
CERTIFICATE OF CORRECTION

PATENT NO. : 5,260,208
DATED : November 9, 1993
INVENTOR(S) : Dominique PETRE et al.

It is certified that error appears in the above-indentified patent and that said Letters Patent is hereby corrected as shown below:

Columns 15-18, SEQ ID NO:1 (2)(i)(A), change "1878" to --1879--;
between nucleotides at positions 801 and 802, add --T--;
change nucleotides 1462-1464 from "GCG" to --CGC--.

SEQ ID NO:2 (2)(i)(A), change "503" to --521--;
after amino acid position 11, insert --Asp Ala Ala Ala Arg
His Tyr Gly Ile Thr Leu Asp Lys Thr Ala Arg Leu Glu--.
Columns 21 and 22,
SEQ ID NO:3 (2)(i)(A), change "1817" to --1816--;
at nucleotide position 1304, delete "G".

Column 29, SEQ ID NO:17, at nucleotide position 6, change "C" to --G--.

Signed and Sealed this

Thirty-first Day of May, 1994

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 1878 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
CGATCCGGAA  ACAGTACTTC  GGCAGCTTGC  CACGACACCG  AAAAGCTCTA  CGAACACCGG      60

TGTTCCACTG  CATCGGCCGA  TTCTGATCGC  TGAATCGGCC  CGTGGGCGAC  TGTACCCCCG     120

CTCTCTCTGA  GCGCACGTAA  CCCGAACTTA  ACGAGTCAAT  ATGTCGATAC  CTATTGACGC     180

AATTATGGAT  CCGGCCCTAG  TCTGAAAGAC  AAGTGAAGCC  GATCACATCA  GGAGCACACT     240
```

-continued

| | | | | |
|---|---|---|---|---|
| TCTCATGGCG | ACAATCCGAC | CTGACGACAA | AGCAATAGAC | GCCGCCGCAA GGCATTACGG | 300 |
| CATCACTCTC | GACAAAACAG | CCCGGCTCGA | GTGGCCGGCA | CTGATCGACG GAGCACTGGG | 360 |
| CTCCTACGAC | GTCGTCGACC | AGTTGTACGC | CGACGAGGCG | ACCCCGCCGA CCACGTCACG | 420 |
| CGAGCACGCG | GTGCCAAGTG | CGAGCGAAAA | TCCTTTGAGC | GCTTGGTATG TGACCACCAG | 480 |
| CATCCCGCCG | ACGTCGGACG | GCGTCCTGAC | CGGCCGACGC | GTGGCGATCA AGGACAACGT | 540 |
| GACCGTGGCC | GGAGTTCCGA | TGATGAACGG | ATCTCGGACG | GTAGAGGGAT TTACTCCGTC | 600 |
| ACGCGACGCG | ACTGTGGTCA | CTCGACTACT | GGCGGCCGGT | GCAACCGTCG CGGGCAAAGC | 660 |
| TGTGTGTGAG | GACCTGTGTT | CTCCGGTTC | GAGCTTCACA | CCGGCAAGCG GACCGGTCCG | 720 |
| CAATCCATGG | GACCGGCAGC | GCGAAGCAGG | TGGATCATCC | GGCGGCAGTG CAGCACTCGT | 780 |
| CGCAAACGGT | GACGTCGATT | TGCCATCGGC | GGGGATCAAG | GCGGATCGAT CCGGATCCCG | 840 |
| GCGGCATTCT | GCGGCGTCGT | CGGGCACAAG | CCGACGTTCG | GGCTCGTCCC GTATACCGGT | 900 |
| GCATTTCCCA | TCGAGCGAAC | AATCGACCAT | CTCGGCCCGA | TCACACGCAC GGTCCACGAT | 960 |
| GCAGCACTGA | TGCTCTCGGT | CATCGCCGGC | CGCGACGGTA | ACGACCCACG CCAAGCCGAC | 1020 |
| AGTGTCGAAG | CAGGTGACTA | TCTGTCCACC | CTCGACTCCG | ATGTGGACGG CCTGCGAATC | 1080 |
| GGAATCGTTC | GAGAGGGATT | CGGGCACGCG | GTCTCACAGC | CCGAGGTCGA CGACGCAGTC | 1140 |
| CGCGCAGCGG | CACACAGTCT | GACCGAAATC | GGTTGCACGG | TAGAGGAAGT AAACATCCCG | 1200 |
| TGGCATCTGC | ATGCTTTCCA | CATCTGGAAC | GTGATCGCCA | CGGACGGTGG TGCCTACCAG | 1260 |
| ATGTTGGACG | GCAACGGATA | CGGCATGAAC | GCCGAAGGTT | TGTACGATCC GGAACTGATG | 1320 |
| GCACACTTTG | CTTCTCGACG | CATTCAGCAC | GCCGACGCTC | TGTCCGAAAC CGTCAAACTG | 1380 |
| GTGGCCCTGA | CCGGCCACCA | CGGCATCACC | ACCCTCGGCG | GCGCGAGCTA CGGCAAAGCC | 1440 |
| CGGAACCTCG | TACCGCTTGC | CGCGGCCGCC | TACGACACTG | CCTTGAGACA ATTCGACGTC | 1500 |
| CTGGTGATGC | CAACGCTGCC | CTACGTCGCA | TCCGAATTGC | CGGCGAAGGA CGTAGATCGT | 1560 |
| GCAACCTTCA | TCACCAAGGC | TCTCGGGATG | ATCGCCAACA | CGGCACCATT CGACGTGACC | 1620 |
| GGACATCCGT | CCCTGTCCGT | TCCGGCCGGC | CTGGTGAACG | GGCTTCCGGT CGGAATGATG | 1680 |
| ATCACCGGCA | GACACTTCGA | CGATGCGACA | GTCCTTCGTG | TCGGACGCGC ATTCGAAAAG | 1740 |
| CTTCGCGGCG | CGTTTCCGAC | GCCGGCCGAA | CGCGCCTCCA | ACTCTGCACC ACAACTCAGC | 1800 |
| CCCGCCTAGT | CCTGACGCAC | TGTCAGACAA | CAAATTCCAC | CGATTCACAC ATGATCAGCC | 1860 |
| CACATAAGAA | AAGGTGAA | | | | 1878 |

( 2 ) INFORMATION FOR SEQ ID NO:2:

( i ) SEQUENCE CHARACTERISTICS:
        ( A ) LENGTH: 503 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Thr Ile Arg Pro Asp Asp Lys Ala Ile Trp Pro Ala Leu Ile
 1               5                  10                  15

Asp Gly Ala Leu Gly Ser Tyr Asp Val Val Asp Gln Leu Tyr Ala Asp
            20                  25                  30

Glu Ala Thr Pro Pro Thr Thr Ser Arg Glu His Ala Val Pro Ser Ala
        35                  40                  45

Ser Glu Asn Pro Leu Ser Ala Trp Tyr Val Thr Thr Ser Ile Pro Pro
    50                  55                  60

Thr Ser Asp Gly Val Leu Thr Gly Arg Arg Val Ala Ile Lys Asp Asn
65                  70                  75                  80
```

| | | | | | | | | | | | | | |
|---|---|---|---|---|---|---|---|---|---|---|---|---|---|
|Val|Thr|Val|Ala|Gly<br>85|Val|Pro|Met|Met|Asn<br>90|Gly|Ser|Arg|Thr|Val<br>95|Glu|
|Gly|Phe|Thr|Pro<br>100|Ser|Arg|Asp|Ala|Thr<br>105|Val|Val|Thr|Arg|Leu<br>110|Leu|Ala|
|Ala|Gly|Ala<br>115|Thr|Val|Ala|Gly|Lys<br>120|Ala|Val|Cys|Glu|Asp<br>125|Leu|Cys|Phe|
|Ser|Gly<br>130|Ser|Ser|Phe|Thr|Pro<br>135|Ala|Ser|Gly|Pro|Val<br>140|Arg|Asn|Pro|Trp|
|Asp<br>145|Arg|Gln|Arg|Glu|Ala<br>150|Gly|Ser|Ser|Gly<br>155|Gly|Ser|Ala|Ala|Leu<br>160|
|Val|Ala|Asn|Gly|Asp<br>165|Val|Asp|Phe|Ala|Ile<br>170|Gly|Gly|Asp|Gln|Gly<br>175|Gly|
|Ser|Ile|Arg|Ile<br>180|Pro|Ala|Ala|Phe|Cys<br>185|Gly|Val|Val|Gly|His<br>190|Lys|Pro|
|Thr|Phe|Gly<br>195|Leu|Val|Pro|Tyr|Thr<br>200|Gly|Ala|Phe|Pro|Ile<br>205|Glu|Arg|Thr|
|Ile|Asp<br>210|His|Leu|Gly|Pro|Ile<br>215|Thr|Arg|Thr|Val|His<br>220|Asp|Ala|Ala|Leu|
|Met<br>225|Leu|Ser|Val|Ile|Ala<br>230|Gly|Arg|Asp|Gly|Asn<br>235|Asp|Pro|Arg|Gln|Ala<br>240|
|Asp|Ser|Val|Glu|Ala<br>245|Gly|Asp|Tyr|Leu|Ser<br>250|Thr|Leu|Asp|Ser|Asp<br>255|Val|
|Asp|Gly|Leu|Arg<br>260|Ile|Gly|Ile|Val|Arg<br>265|Glu|Gly|Phe|Gly|His<br>270|Ala|Val|
|Ser|Gln|Pro<br>275|Glu|Val|Asp|Asp|Ala<br>280|Val|Arg|Ala|Ala|Ala<br>285|His|Ser|Leu|
|Thr|Glu<br>290|Ile|Gly|Cys|Thr|Val<br>295|Glu|Glu|Val|Asn|Ile<br>300|Pro|Trp|His|Leu|
|His<br>305|Ala|Phe|His|Ile|Trp<br>310|Asn|Val|Ile|Ala|Thr<br>315|Asp|Gly|Gly|Ala|Tyr<br>320|
|Gln|Met|Leu|Asp|Gly<br>325|Asn|Gly|Tyr|Gly|Met<br>330|Asn|Ala|Glu|Gly|Leu<br>335|Tyr|
|Asp|Pro|Glu|Leu<br>340|Met|Ala|His|Phe|Ala<br>345|Ser|Arg|Arg|Ile|Gln<br>350|His|Ala|
|Asp|Ala|Leu<br>355|Ser|Glu|Thr|Val|Lys<br>360|Leu|Val|Ala|Leu|Thr<br>365|Gly|His|His|
|Gly|Ile<br>370|Thr|Thr|Leu|Gly|Gly<br>375|Ala|Ser|Tyr|Gly|Lys<br>380|Ala|Arg|Asn|Leu|
|Val<br>385|Pro|Leu|Ala|Arg|Ala<br>390|Ala|Tyr|Asp|Thr|Ala<br>395|Leu|Arg|Gln|Phe|Asp<br>400|
|Val|Leu|Val|Met|Pro<br>405|Thr|Leu|Pro|Tyr|Val<br>410|Ala|Ser|Glu|Leu|Pro<br>415|Ala|
|Lys|Asp|Val|Asp<br>420|Arg|Ala|Thr|Phe|Ile<br>425|Thr|Lys|Ala|Leu|Gly<br>430|Met|Ile|
|Ala|Asn|Thr<br>435|Ala|Pro|Phe|Asp|Val<br>440|Thr|Gly|His|Pro|Ser<br>445|Leu|Ser|Val|
|Pro|Ala<br>450|Gly|Leu|Val|Asn|Gly<br>455|Leu|Pro|Val|Gly|Met<br>460|Met|Ile|Thr|Gly|
|Arg<br>465|His|Phe|Asp|Asp|Ala<br>470|Thr|Val|Leu|Arg|Val<br>475|Gly|Arg|Ala|Phe|Glu<br>480|
|Lys|Leu|Arg|Gly|Ala<br>485|Phe|Pro|Thr|Pro|Ala<br>490|Glu|Arg|Ala|Ser|Asn<br>495|Ser|
|Ala|Pro|Gln|Leu<br>500|Ser|Pro|Ala| | | | | | | | |

( 2 ) INFORMATION FOR SEQ ID NO:3:

( i ) SEQUENCE CHARACTERISTICS:
        ( A ) LENGTH: 1817 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| CTGCAGAACG | GAACTAAGAT | GGCTCGAACC | TTCACCAAAG | ACGGACTTGA | ACACAGCCTC | 60 |
| GCACTTGCGC | GTTTGGAGCT | CCCGGACGAG | CGTTACGAGA | CGGTGACAGC | GGCTGCCGAG | 120 |
| TTGGTCCTCG | GACTCGCTGA | GGCTCTGGAT | GCTGTCCCGC | TGGCCGAGAC | TCCGATGGCA | 180 |
| GCCGCCTTCG | ATGCGCGGTG | GGAGTGACGA | TGGGCTTGCA | TGAACTGACG | CTCGCGCAAG | 240 |
| TCGCTGCGAA | GATCGAGAAC | AAAGAACTTT | CCCCGGTCGA | GCTCCTCGAT | GTGATCCTGG | 300 |
| CGCGCGTCGC | GGAGATCGAA | CCGAAGATCT | CCGCCTTCGT | CACGATCACC | GCCGATTCCG | 360 |
| CTCGGAAGGC | GGCCCGGCTC | GCAGCCGACG | AGATCGCAGG | TGGGCACTAT | CGCGGTCCGC | 420 |
| TGCACGGAGT | TCCGATTGGC | CTCAAGGATC | TGTTCGAAGT | GGCAGGCGTC | CCGAATACCG | 480 |
| CGAGTTCGCG | GGTCCGAGCT | GACTACATCC | CCTCATCGGA | TGGGGCCGCG | GTCGAGAAGC | 540 |
| TCACCGCCGG | TGGAGCGGTC | ATGATCGGCA | AGACGCACAC | TCACGAATTC | GCCTACGGTG | 600 |
| CGATCACACC | GACCACCCGT | AATCCATGGG | ACCCCACCCG | GACACCGGC | GGTTCCAGCG | 660 |
| GTGGGACGGC | AGCAGCTCTC | GCGGCAGGCC | TCATCTTCGC | CGGTATGGGT | ACCGATACCG | 720 |
| GGGGGTCCAT | TCGGATACCA | GCCGCCGTCT | GCGGGACGGT | AGGTCTCAAA | CCCACATATG | 780 |
| GTCGCGTTTC | GCGTCGTGGA | GTGACCTCCT | TGTCATGGTC | TCTGGACCAC | GCGGGACCGC | 840 |
| TGGCCCGGAC | CGTGGAAGAC | GCTGCCATCA | TGCTGAACCA | GATCGCTGGC | TATGACCGGG | 900 |
| CTGATCCTGC | GACGGTAGAT | GTGCCCGTTC | CCGACTACGC | GGCGGCGCTG | ACCGGAGACG | 960 |
| TCCGAGGGCT | GCGGATTGGT | GTGCCGACCA | ATTTCTACAC | CGACAACGTC | CATCCCGAGG | 1020 |
| TTGCCGCAGC | GGCCGACGCT | GCGGTGGCGC | AACTGGCCCA | TTTGGGTGCG | GTGGTCCGCG | 1080 |
| AAGTGAAGAT | CCCGATGGCA | GAGGTCATCG | TGCCCACCGA | GTGGAGCTTG | CTCGTCCCGG | 1140 |
| AGGCGTCGGC | CTACCACCAG | CAGATGCTGC | GCGAGCGCGC | AGATCACTAC | ACCGACGAGA | 1200 |
| CGAGAACCTT | CCTGGAAGCC | GGCGAACTCG | TTCCGGCGAC | CGACTACATC | AAGGCGCTGC | 1260 |
| GGGTGCGCAC | CCTCATCCAG | GCAGCCTTCC | GGGGAACTGT | TCCAGGACAT | CGATGTCCTG | 1320 |
| ATCGCACCCA | CGGTCAGCTC | TCCGGCTCTG | CCGCTCGATG | ACCTGGAAGT | CACTTGGCCC | 1380 |
| GATGGCACAT | CCGAAGGCGG | CACCATCACC | TATGTCCGTC | TCAGCGCCCC | CGGCAACGTC | 1440 |
| ACCGGACTTC | CAGCGCTGTC | GGTCCCCTCC | GGCTTCACCG | AGCAAGGCCT | TCCCACCGGT | 1500 |
| ATCCAGATCA | TCGGCCGTCC | CTTCGACGAG | GAGACCGTCC | TCAACGTCGG | TCACGCCTAC | 1560 |
| GAAGGCTGCA | CGGACTGGCC | GCGACTGGCG | CCGCTTTGAA | CTACTGACCC | CCATTGGAGA | 1620 |
| AAACCGAAGG | AGAGAACGAT | GAATGGAGTG | TTCGATTTGG | GTGGGACCGA | CGGCATCGGC | 1680 |
| CCGGTCGACC | CTCCCGCTGA | AGAACCGGTG | TTCCGCGCGG | ACTGGGAGAA | AGCAGCCTTC | 1740 |
| ACCATGTTCT | CGGCGCTATT | CCGTGCCGGC | TGGTTCGGCA | TCGACGAATT | CCGTCACGGT | 1800 |
| GTCGAAAAGA | TGGATCC | | | | | 1817 |

( 2 ) INFORMATION FOR SEQ ID NO:4:

( i ) SEQUENCE CHARACTERISTICS:
        ( A ) LENGTH: 462 amino acids
        ( B ) TYPE: amino acid
        ( D ) TOPOLOGY: linear (i i) MOLECULE TYPE: protein (x i) SEQUENCE DESCRIPTION: SEQ ID NO:4:

```
Met Gly Leu His Glu Leu Thr Leu Ala Gln Val Ala Ala Lys Ile Glu
 1               5                  10                  15

Asn Lys Glu Leu Ser Pro Val Glu Leu Asp Val Ile Leu Ala Arg
            20                  25                  30

Val Ala Glu Ile Glu Pro Lys Ile Ser Ala Phe Val Thr Ile Thr Ala
            35                  40                  45

Asp Ser Ala Arg Lys Ala Ala Arg Leu Ala Ala Asp Glu Ile Ala Gly
    50                  55                  60

Gly His Tyr Arg Gly Pro Leu His Gly Val Pro Ile Gly Leu Lys Asp
65                  70                  75                  80

Leu Phe Glu Val Ala Gly Val Pro Asn Thr Ala Ser Ser Arg Val Arg
                85                  90                  95

Ala Asp Tyr Ile Pro Ser Ser Asp Gly Ala Ala Val Glu Lys Leu Thr
                100                 105                 110

Ala Gly Gly Ala Val Met Ile Gly Lys Thr His Thr His Glu Phe Ala
            115                 120                 125

Tyr Gly Ala Ile Thr Pro Thr Thr Arg Asn Pro Trp Asp Pro Thr Arg
    130                 135                 140

Thr Pro Gly Gly Ser Ser Gly Gly Thr Ala Ala Ala Leu Ala Ala Gly
145                 150                 155                 160

Leu Ile Phe Ala Gly Met Gly Thr Asp Thr Gly Gly Ser Ile Arg Ile
                165                 170                 175

Pro Ala Ala Val Cys Gly Thr Val Gly Leu Lys Pro Thr Tyr Gly Arg
                180                 185                 190

Val Ser Arg Arg Gly Val Thr Ser Leu Ser Trp Ser Leu Asp His Ala
        195                 200                 205

Gly Pro Leu Ala Arg Thr Val Glu Asp Ala Ala Ile Met Leu Asn Gln
    210                 215                 220

Ile Ala Gly Tyr Asp Arg Ala Asp Pro Ala Thr Val Asp Val Pro Val
225                 230                 235                 240

Pro Asp Tyr Ala Ala Ala Leu Thr Gly Asp Val Arg Gly Leu Arg Ile
                245                 250                 255

Gly Val Pro Thr Asn Phe Tyr Thr Asp Asn Val His Pro Glu Val Ala
            260                 265                 270

Ala Ala Ala Asp Ala Ala Val Ala Gln Leu Ala His Leu Gly Ala Val
            275                 280                 285

Val Arg Glu Val Lys Ile Pro Met Ala Glu Val Ile Val Pro Thr Glu
    290                 295                 300

Trp Ser Leu Leu Val Pro Glu Ala Ser Ala Tyr His Gln Gln Met Leu
305                 310                 315                 320

Arg Glu Arg Ala Asp His Tyr Thr Asp Glu Thr Arg Thr Phe Leu Glu
                325                 330                 335

Ala Gly Glu Leu Val Pro Ala Thr Asp Tyr Ile Lys Ala Leu Arg Val
            340                 345                 350

Arg Thr Leu Ile Gln Ala Ala Phe Arg Glu Leu Phe Gln Asp Ile Asp
        355                 360                 365

Val Leu Ile Ala Pro Thr Val Ser Ser Pro Ala Leu Pro Leu Asp Asp
    370                 375                 380

Leu Glu Val Thr Trp Pro Asp Gly Thr Ser Glu Gly Gly Thr Ile Thr
385                 390                 395                 400

Tyr Val Arg Leu Ser Ala Pro Gly Asn Val Thr Gly Leu Pro Ala Leu
                405                 410                 415
```

```
    Ser  Val  Pro  Ser  Gly  Phe  Thr  Glu  Gln  Gly  Leu  Pro  Thr  Gly  Ile  Gln
                   420                      425                     430

Ile  Ile  Gly  Arg  Pro  Phe  Asp  Glu  Glu  Thr  Val  Leu  Asn  Val  Gly  His
                   435                      440                     445

Ala  Tyr  Glu  Gly  Cys  Thr  Asp  Trp  Pro  Arg  Leu  Ala  Pro  Leu
              450                      455                     460
```

( 2 ) INFORMATION FOR SEQ ID NO:5:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
    Ala  Thr  Ile  Arg  Pro  Asp  Asp  Lys  Ala  Ile  Asp  Ala  Ala  Ala  Arg  His
    1                   5                        10                       15

Tyr  Gly  Ile  Thr  Leu  Asp  Lys  Thr  Ala  Arg  Leu
                   20                       25
```

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
    Leu  Glu  Trp  Pro  Ala  Leu  Ile  Asp  Gly  Ala  Leu  Gly  Ser  Tyr  Asp  Val
    1                   5                        10                       15

Val  Asp  Gln  Leu  Tyr
                   20
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
    Ile  Asp  Gly  Ala  Leu  Gly  Ser  Tyr  Asp  Val
    1                   5                        10
```

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATCGATGGCG CCCTCGGCTC CTACGATGT                                              29

( 2 ) INFORMATION FOR SEQ ID NO:9:

( i ) SEQUENCE CHARACTERISTICS:
        ( A ) LENGTH: 29 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:9:

ACGTCGTAGG AGCCGAGGGC GCCGTCGAT 29

(2) INFORMATION FOR SEQ ID NO:10:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

CCAAGCTTGC TGTTTTGTCA AGCGTGATGC CGTAATGCCT TGCGGCGGCG TCTATTGCTT 60

TGTC 64

(2) INFORMATION FOR SEQ ID NO:11:

(i) SEQUENCE CHARACTERISTICS:
(A) LENGTH: 57 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

GACAAAGCAA TAGACGCCGC CGCAAGGCAT TACGGCATCA CGCTTGACCA AAACAGC 57

(2) INFORMATION FOR SEQ ID NO:12:

(i) SEQUENCE CHARACTERISTICS:
(A) LENGTH: 18 amino acids
(B) TYPE: amino acid
(D) TOPOLOGY: linear (ii) MOLECULE TYPE: protein (xi) SEQUENCE DESCRIPTION: SEQ ID NO:12:

Thr Lys Asp Leu Thr Ile Gly Tyr His Arg Ala Ala Ala Asp Ile Ala
1               5                   10                  15
Lys Asp (2) INFORMATION FOR SEQ ID NO:13:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GTCTGGTCGA ATGGTAGC 18

(2) INFORMATION FOR SEQ ID NO:14:

(i) SEQUENCE CHARACTERISTICS:
(A) LENGTH: 26 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:14:

CGGAATTCGC TACCATTCGA CCAGAC                                              26

(2) INFORMATION FOR SEQ ID NO:15:

(i) SEQUENCE CHARACTERISTICS:
      (A) LENGTH: 6 amino acids
      (B) TYPE: amino acid
      (D) TOPOLOGY: linear (ii) MOLECULE TYPE: protein (xi) SEQUENCE DESCRIPTION: SEQ ID NO:15:

Asp Pro Arg Ile Thr Ala
1               5

(2) INFORMATION FOR SEQ ID NO:16:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:16:

GATGCCGTAA TGCCTTGCGG CGGCGTCTAT TGCTTTGTCG                                40

(2) INFORMATION FOR SEQ ID NO:17:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:17:

GCNACNGTNG ATGTNCCNGT NCCNGATTAT GC                                        32